(12) United States Patent
Mueller et al.

(10) Patent No.: US 11,103,391 B2
(45) Date of Patent: Aug. 31, 2021

(54) ABSORBENT ARTICLE WITH FASTENING SYSTEM

(71) Applicant: The Procter & Gamble Company, Cincinnati, OH (US)

(72) Inventors: Joerg Mueller, Karben (DE); Gabrielle Elisabeth Krallmann, Frankfurt (DE); Darren Lee Goad, Cold Spring, KY (US); Anja Schuehle, Hofheim (DE); Fang Liu, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1176 days.

(21) Appl. No.: 15/475,299

(22) Filed: Mar. 31, 2017

(65) Prior Publication Data
US 2017/0281428 A1    Oct. 5, 2017

Related U.S. Application Data

(60) Provisional application No. 62/316,656, filed on Apr. 1, 2016.

(51) Int. Cl.
*A61F 13/58*    (2006.01)
*A61F 13/62*    (2006.01)

(52) U.S. Cl.
CPC .......... *A61F 13/581* (2013.01); *A61F 13/622* (2013.01); *A61F 13/627* (2013.01); *A61F 2013/583* (2013.01)

(58) Field of Classification Search
CPC ........ A61F 13/5148; A61F 2013/51411; A61F 2013/51443; A61F 13/514; A61F 13/581; A61F 13/622; A61F 2013/588; A61F 2013/586; A61F 13/58; A61F 2013/51409; A61F 2013/5147; A61F 13/51498
See application file for complete search history.

(56) References Cited

U.S. PATENT DOCUMENTS

| | | | |
|---|---|---|---|
| 3,860,003 A | | 1/1975 | Buell |
| 4,210,144 A | * | 7/1980 | Sarge, III ................ A61F 13/58 604/365 |
| 4,710,190 A | * | 12/1987 | Wood ...................... A61F 13/58 604/389 |
| 5,061,262 A | * | 10/1991 | Chen ....................... A61F 13/58 604/389 |
| 5,147,346 A | | 9/1992 | Cancio et al. |

(Continued)

OTHER PUBLICATIONS

PCT International Search Report, dated May 30, 2017 (14 pages).

*Primary Examiner* — Michele M Kidwell
(74) *Attorney, Agent, or Firm* — Daniel S. Albrecht; William E. Gallagher; Andrew J. Mueller

(57) ABSTRACT

An absorbent article includes a chassis having i) a topsheet, ii) a backsheet comprising a film layer and an outer cover layer, and iii) an absorbent core disposed between the topsheet and the backsheet; and a fastening system, the fastening system having a male fastener and a female fastening material, wherein the female fastening material is comprised of a portion of the outer cover layer that is located in a landing zone area; wherein the film layer and the outer cover layer are joined together through a backsheet adhesive applied in a first pattern; and in the landing zone area, the film layer and the outer cover layer are joined together through an additional LZA adhesive applied in a second pattern.

21 Claims, 27 Drawing Sheets

(56) References Cited

U.S. PATENT DOCUMENTS

| | | |
|---|---|---|
| 5,433,715 A | 7/1995 | Tanzer |
| 5,580,411 A | 12/1996 | Nease |
| 5,599,335 A | 2/1997 | Goldman |
| 5,607,414 A | 3/1997 | Richards |
| 5,700,254 A | 12/1997 | McDowall |
| 5,843,056 A * | 12/1998 | Good ................ A61F 13/5148 604/367 |
| 5,843,057 A * | 12/1998 | McCormack .......... A41D 31/02 604/367 |
| 5,843,066 A | 12/1998 | Dobrin |
| 5,846,365 A | 12/1998 | Kline et al. |
| 6,004,306 A | 12/1999 | Robles et al. |
| 6,534,149 B1 | 3/2003 | Daley |
| 6,544,244 B1 * | 4/2003 | Glaug .................... A61F 13/60 604/389 |
| 6,632,504 B1 | 10/2003 | Gillespie |
| 7,750,203 B2 | 7/2010 | Becker |
| 9,295,593 B2 | 3/2016 | VanMalderen |
| 9,408,761 B2 | 8/2016 | Xu |
| 9,804,701 B2 | 10/2017 | Westerman et al. |
| 2002/0123728 A1 | 9/2002 | Graef |
| 2008/0312622 A1 | 12/2008 | Hundorf |

* cited by examiner

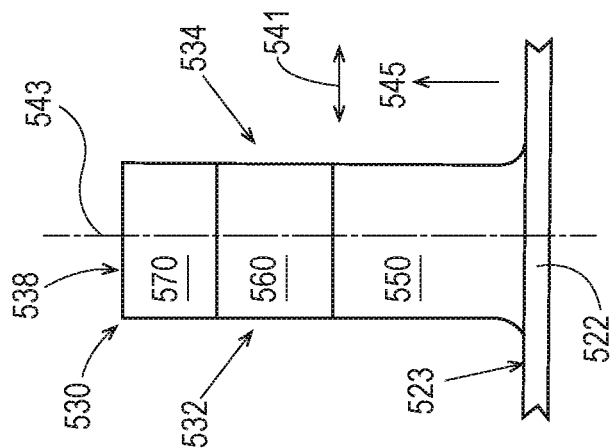
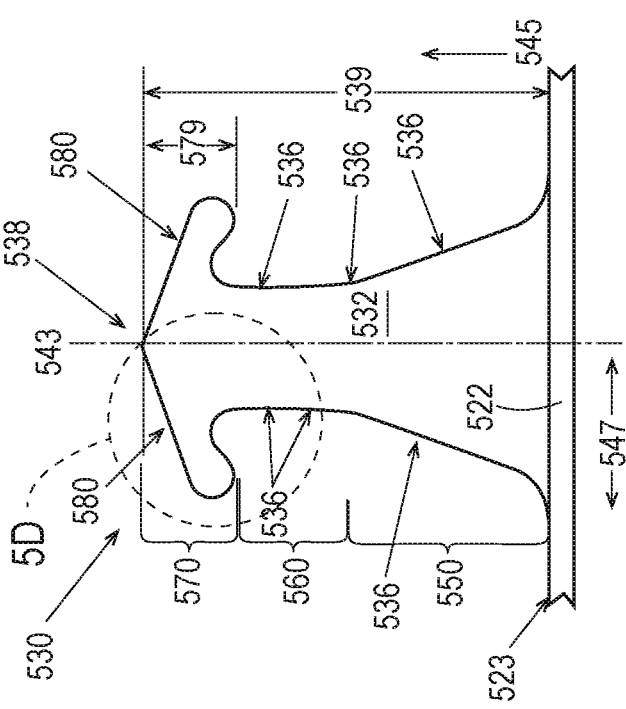
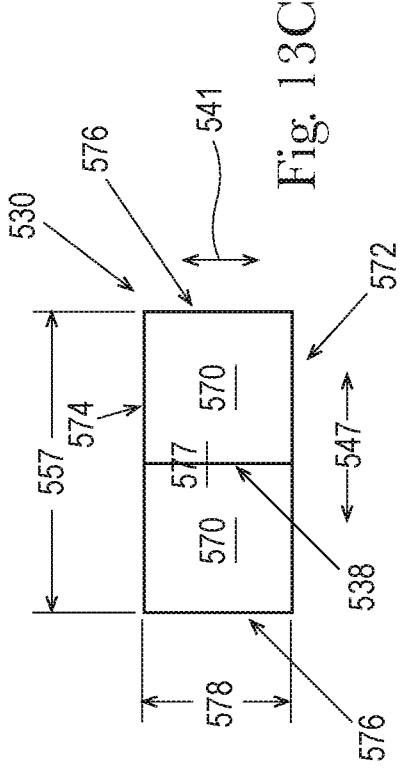
Fig. 13A
Fig. 13B
Fig. 13C

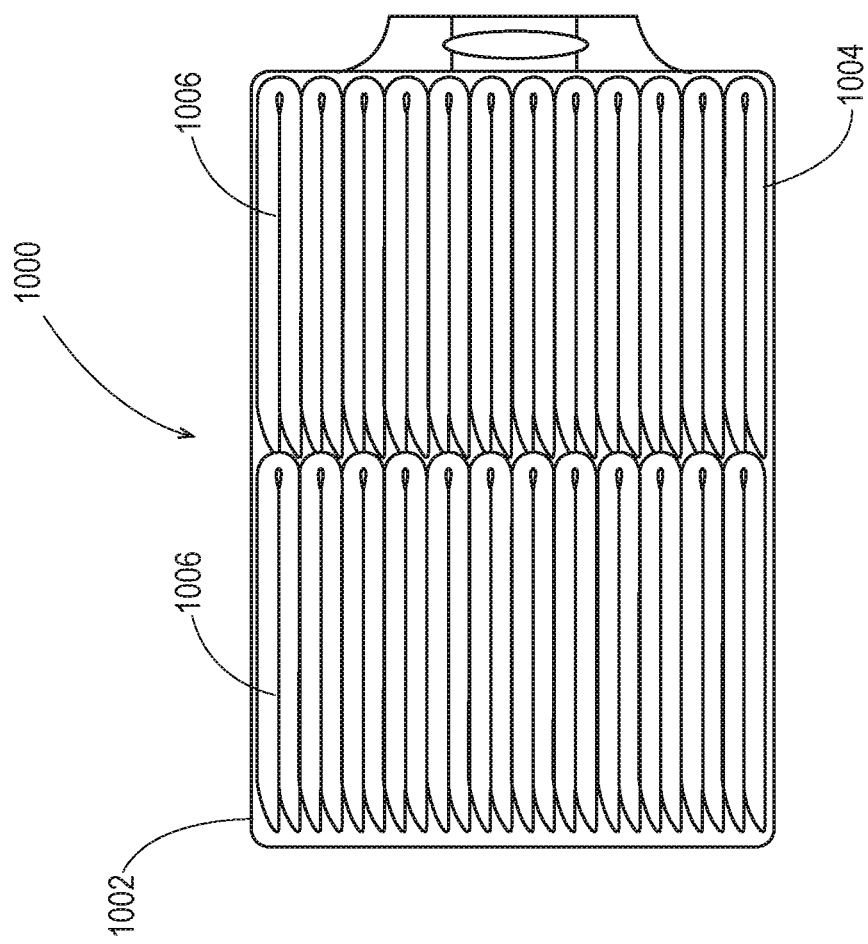

ABSORBENT ARTICLE WITH FASTENING SYSTEM

CROSS REFERENCE TO RELATED APPLICATION

This application claims the benefit of U.S. Provisional Application No. 62/316,656, filed Apr. 1, 2016, the substance of which is incorporated herein by reference.

FIELD

The present disclosure is generally related to disposable absorbent articles, and is more specifically related to disposable absorbent articles with improved fastening systems, aesthetics and manufacturing process reliability.

BACKGROUND

It is known to use fastening systems to secure the corners of disposable absorbent articles, such as diapers and adult incontinence articles. Such fastening systems are used to provide a secure means for keeping such articles on the wearer during use. When such fastening systems are refastenable, adjustments may be made during use to reposition the articles, to allow a caregiver to check for soiling, and to provide a secure means for keeping such articles and their soiled contents wrapped up after use until disposal.

A traditional fastening system for use with disposable absorbent articles has a male fastener and a female fastening material. The male fastener may be disposed directly or indirectly upon the longitudinal edge of the chassis in either the front or back of the absorbent article waist regions. In use, the male fastener may be secured to the female fastening material, which is disposed upon the correspondingly opposite body portion of the front or back of the absorbent article. An exemplary fastener system that is refastenable may be provided with hooks on the male fastener that releasably engage loops on the female fastening material (i.e., a landing zone member), or vice versa. To improve fit, the end of the male fastener that does not engage the loops of the female fastening material, may be attached to one end of an elastically elongatable panel (i.e., a stretch back ear), and the other end of the elastically elongatable panel may be secured to the longitudinal edge of the chassis of the disposable absorbent article.

Such female fastening materials often take the form of an attached separate landing zone member that is disposed centrally on the front of a disposable absorbent article. In certain embodiments, the female fastening material can disrupt (e.g., be placed over) the artwork on the front of the diaper. Accordingly, a disposable absorbent article that includes a suitable fastening system that does not disrupt the artwork on the front of the article is of continued interest.

Further, manufacturers of disposable absorbent articles typically employ mechanical assembly lines in which a variety of absorbent article components are fed into a linear process whereby each additional manufacturing step builds upon the last one. Such assembly lines are often referred to as "converters." As the partially constructed absorbent article progresses towards the end of the converter, it becomes more complete, until at the end of the line, all the necessary parts have been provided and arranged as needed to yield a completely assembled disposable absorbent article. The process is typically automated and may be controlled by various computer programs and/or human operators, as desired. In order to make the manufacture of absorbent articles economically viable, such converting lines must be capable of operating at high speeds with good repeatability and consistency between consecutive articles. Two elements that impact economic viability are 1) the nature of the disposable absorbent article components and how they will be attached to other components to form a completely assembled absorbent article, and 2) the material cost of each absorbent article component. Accordingly, a disposable absorbent article that includes a suitable fastening system and can be manufactured more economically and reliably is of continued interest.

Further, if the fastening system is refastenable, after the male and female fasteners engage and disengage multiple times, the fibers that make up the female fastener may start to disintegrate and form fuzz on the female fastener surface that engages the male fastener. Accordingly, a disposable absorbent article that includes a suitable fastening system that has a female fastener that does not significantly disintegrate after multiple engagements and disengagements with the male fastener is of continued interest.

Disposable absorbent articles with various fastening systems are known in the art. And although fastening systems with integral landing zone members (e.g., the landing zone member is formed from the backsheet material) are known, it is of continued interest to be able to obtain a disposable absorbent article with an integral landing zone member that overcomes the issues detailed above, while also achieving the desired article performance (e.g., secure engagement of fasteners in use, proper article fit, etc.).

SUMMARY

In one aspect, an absorbent article includes a chassis having i) a topsheet, ii) a backsheet comprising a film layer and an outer cover layer, and iii) an absorbent core disposed between the topsheet and the backsheet; a fastening system, the fastening system having a male fastener and a female fastening material, wherein the female fastening material is comprised of a portion of the outer cover layer that is located in a landing zone area; wherein the film layer and the outer cover layer are joined together through a backsheet adhesive applied in a first pattern; and in the landing zone area, the film layer and the outer cover layer are joined together through an additional LZA adhesive applied in a second pattern.

In another aspect, an absorbent article includes a chassis having i) a topsheet, ii) a backsheet comprising a film layer and an outer cover layer, and iii) an absorbent core disposed between the topsheet and the backsheet; a pair of separate, stretchable ears attached to the chassis; and a fastening system, the fastening system having a male fastener and a female fastening material, wherein the female fastening material is comprised of a portion of the outer cover layer that is located in a landing zone area; wherein the film layer and the outer cover layer are joined together through a backsheet adhesive applied in a first pattern; and in the landing zone area, the film layer and the outer cover layer are joined together through an additional LZA adhesive applied in a second pattern; wherein the backsheet adhesive covers between about 30% and about 70% of the surface area of the garment facing surface of the film layer; wherein the backsheet adhesive and the LZA adhesive combine to cover between about 80% and about 100% of the surface area of the garment facing surface of the film layer within the landing zone area.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 13A is an enlarged view of a front of a bidirectional micro-sized hook disposed on a top surface of a substrate of a male fastener;

FIG. 13B is an enlarged side view of the hook of FIG. 13A disposed on the top surface of the substrate;

FIG. 13C is an enlarged top view of the hook of FIG. 13A;

FIG. 22 is a schematic cross sectional view of a package of absorbent articles as detailed herein.

DETAILED DESCRIPTION

Figure 1:
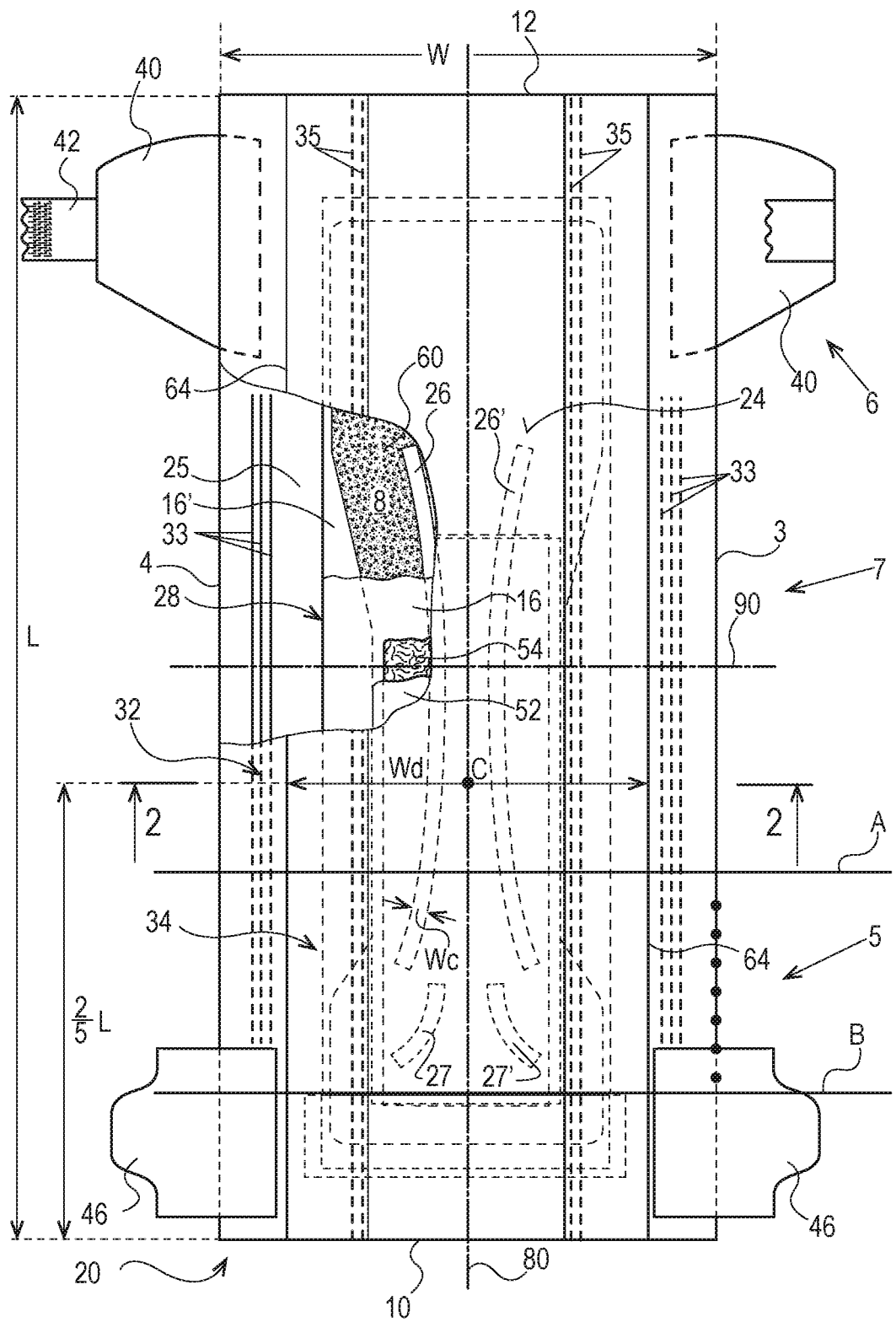
FIG. 1 is a top view of an absorbent article, wearer-facing surface facing the viewer, with some layers partially removed in accordance with the present disclosure.

Various non-limiting embodiments will now be described to provide an overall understanding of the principles of the structure, function, manufacture, and use of the disposable absorbent articles disclosed herein. One or more examples of these non-limiting embodiments are illustrated in the accompanying drawings. Those of ordinary skill in the art will understand that the disposable absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Introduction

As used herein, the term "absorbent article" refers to disposable devices such as infant, child, or adult diapers, adult incontinence products, training pants, sanitary napkins, and the like which are placed against or in proximity to a body of a wearer to absorb and contain the various fluids (urine, menses, and/or runny BM) or bodily exudates (generally solid BM) discharged from the body. Typically, these absorbent articles comprise a topsheet, backsheet, an absorbent core, optionally an acquisition system and/or a distribution system (which may be comprised of one or several layers), and typically other components, with the absorbent core normally placed at least partially between the backsheet and the acquisition and/or distribution system or between the topsheet and the backsheet. Nothing in this description should be, however, considered limiting the scope of the claims. As such the present disclosure applies to any suitable form of absorbent articles (e.g., diapers, training pants, adult incontinence products, sanitary napkins).

As used herein, "bond area percentage" on a nonwoven web is a ratio of area occupied by bond impressions, to the total surface area of the web, expressed as a percentage, and measured according to the Bond Area Percentage Method set forth herein.

As used herein, a "bond impression" in a nonwoven web is the surface structure created by the impression of a bonding protrusion on a calender roller into a nonwoven web. A bond impression is a location of deformed, intermeshed or entangled, and melted or thermally fused, materials from fibers superimposed and compressed in a z-direction beneath the bonding protrusion, which form a bond. The individual bonds may be connected in the nonwoven structure by loose fibres between them. The shape and size of the bond impression approximately corresponds to the shape and size of the bonding surface of a bonding protrusion on the calender roller.

As used herein, a "column" of bonds on a nonwoven web is a group of nearest neighboring bonds of like shape and rotational orientation that are arranged along the line that extends most predominately in the machine direction.

As used herein, the term "nonwoven web" means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yam). Nonwoven webs may be formed by many processes such as meltblowing, spunbonding, solvent spinning, electrospinning, carding, and airlaying. The basis weight of nonwoven webs is usually expressed in grams per square meter ($g/m^2$ or gsm).

As used herein, "volume mass" is the ratio of basis weight and thickness and indicates the bulkiness and fluffiness of the product, which are important properties of the nonwoven web according to the invention. The lower the value, the bulkier is the web:

Volume mass [$kg/m^3$]=basis weight [$g/m^2$]/thickness [mm]

As used herein, "width" or a form thereof, with respect to a diaper or training pant, refers to a dimension measured along a direction parallel to the waist edges and/or perpendicular to the longitudinal axis.

As used herein, the terms "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

General Description of the Absorbent Article

Figure 2:
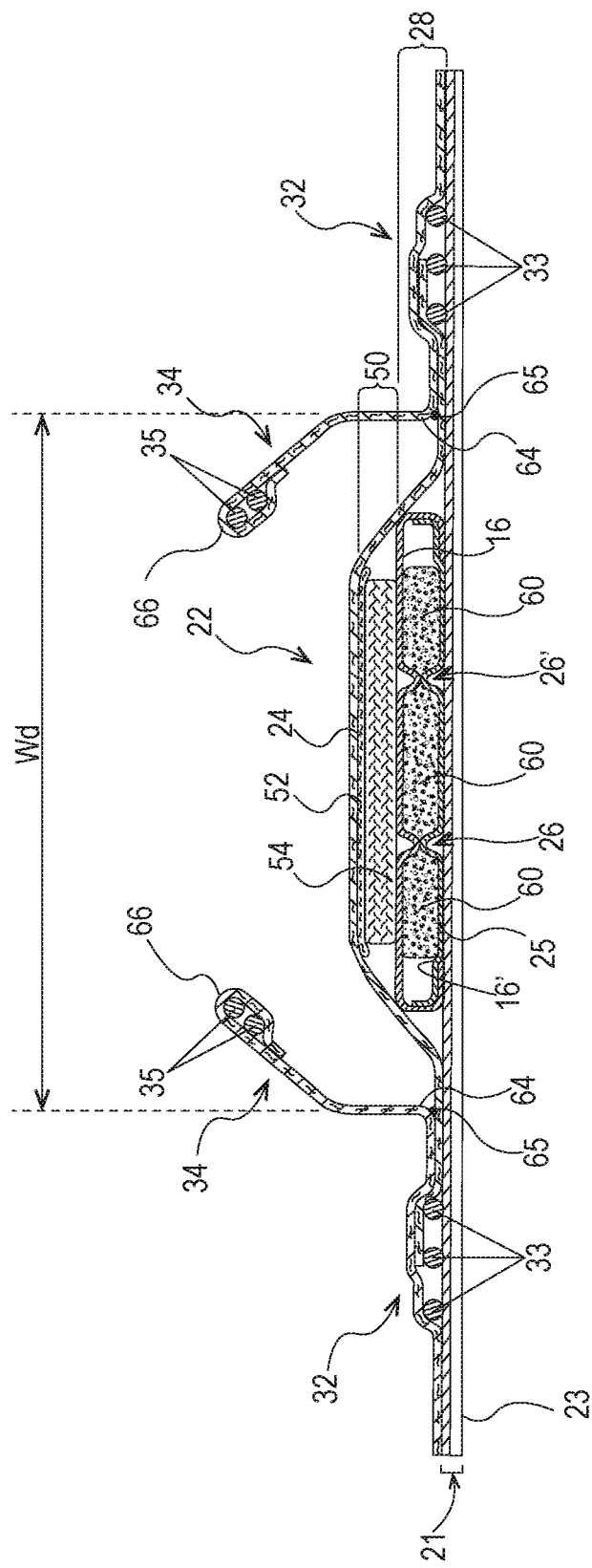
FIG. 2 is a cross-sectional view of the absorbent article taken about line 2-2 of FIG. 1 in accordance with the present disclosure.
Figure 3:
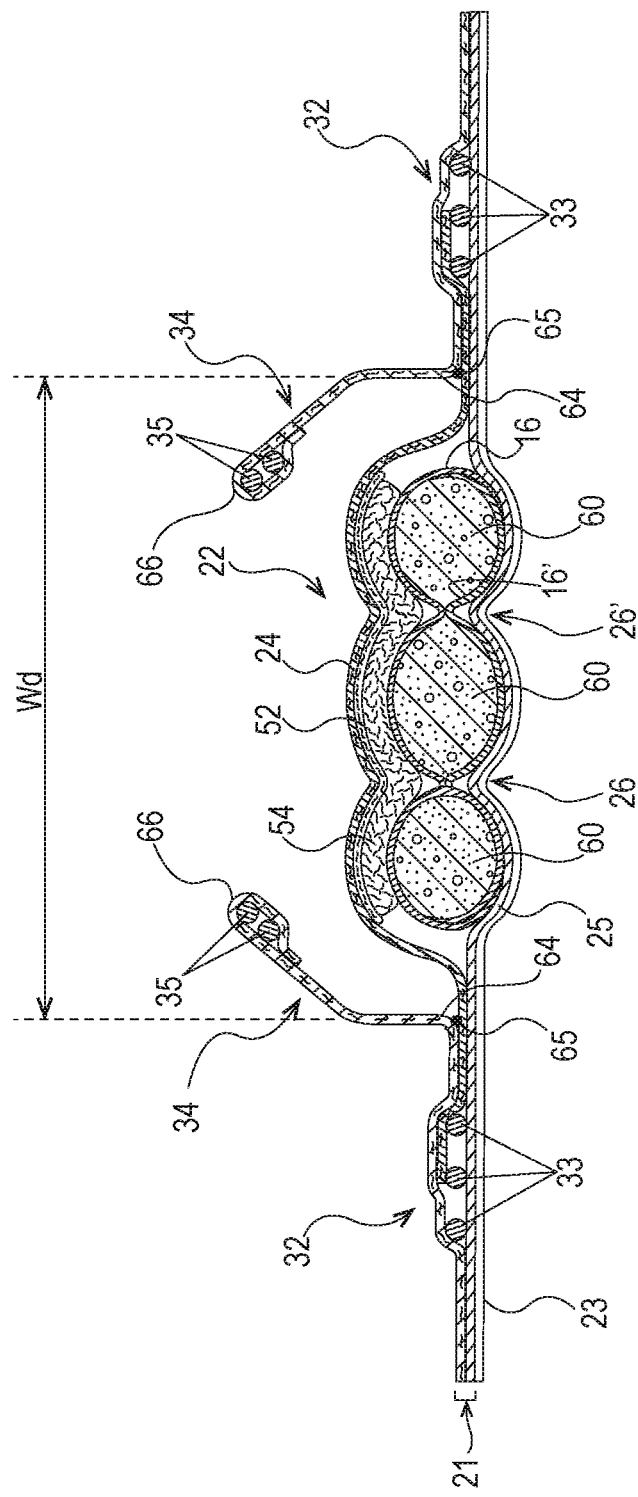
FIG. 3 is a cross-sectional view of the absorbent article taken about line 2-2 of FIG. 2 where the absorbent article has been loaded with fluid in accordance with the present disclosure.

An example absorbent article in the form of a diaper 20 is represented in FIGS. 1-3. FIG. 1 is a plan view of the example diaper 20, in a flat-out state, with portions of the structure being cut-away to more clearly show the construction of the diaper 20. The wearer-facing surface of the diaper 20 of FIG. 1 is facing the viewer.

The absorbent article 20 may comprise a liquid permeable topsheet 24, a liquid impermeable backsheet 21 (including both a film layer 25 and an outer layer 23), an absorbent core 28 positioned at least partially intermediate the topsheet 24 and the backsheet 21, and barrier leg cuffs 34. The absorbent article may also comprise an acquisition and/or distribution system ("ADS") 50, which in the example represented comprises a distribution layer 54 and an acquisition layer 52, which will be further detailed below. The absorbent article may also comprise elasticized gasketing cuffs 32 comprising elastics 33 joined to a chassis of the absorbent article, typically via the topsheet and/or backsheet, and substantially planar with the chassis of the diaper.

The figures also show taped diaper components such as a fastening system comprising a male fastener 42 attached towards the rear edge of the article and cooperating with a portion of the backsheet 21 (the female fastening material being integral with the outer cover 23 of the backsheet 21). The absorbent article may also comprise other elements, which are not represented, such as a rear elastic waist feature, a front elastic waist feature, transverse barrier cuff(s), and/or a lotion application, for example.

The absorbent article 20 comprises a front waist edge 10, a rear waist edge 12 longitudinally opposing the front waist edge 10, a first side edge 3, and a second side edge 4 laterally opposing the first side edge 3. The front waist edge 10 is the edge of the article which is intended to be placed towards the front of the user when worn, and the rear waist edge 12 is the opposite edge. The absorbent article may have a longitudinal axis 80 extending from the lateral midpoint of the front waist edge 10 to a lateral midpoint of the rear waist edge 12 of the article and dividing the article in two substantially symmetrical halves relative to the longitudinal axis 80, with the article placed flat and viewed from above as in FIG. 1. The absorbent article may also have a lateral axis 90 extending from the longitudinal midpoint of the first side edge 3 to the longitudinal midpoint of the second side edge 4. The length, L, of the article may be measured along the longitudinal axis 80 from the front waist edge 10 to the rear waist edge 12. The width, W, of the article may be measured along the lateral axis 90 from the first side edge 3 to the second side edge 4. The article may comprise a crotch point C defined herein as the point placed on the longitudinal axis at a distance of two fifth (⅖) of L starting from the front edge 10 of the article 20. The article may comprise a front waist region 5, a rear waist region 6, and a crotch region 7. The front waist region 5, the rear waist region 6, and the crotch region 7 each define ⅓ of the longitudinal length, L, of the absorbent article.

The topsheet 24, the backsheet 21, the absorbent core 28, and the other article components may be assembled in a variety of configurations, in particular by gluing or heat embossing, for example. Example absorbent article configurations are described generally in U.S. Pat. No. 3,860,003, U.S. Pat. No. 5,221,274, U.S. Pat. No. 5,554,145, U.S. Pat. No. 5,569,234, U.S. Pat. No. 5,580,411, and U.S. Pat. No. 6,004,306.

The absorbent core 28 may comprise an absorbent material comprising at least 80% by weight, at least 90% by weight, at least 95% by weight, or at least 99% by weight of superabsorbent polymers and a core wrap enclosing the superabsorbent polymers. The core wrap may typically comprise two materials, substrates, or nonwoven materials 16 and 16' for the top side and bottom side of the core. The core may comprises one or more channels, represented in FIG. 1 as the four channels 26, 26' and 27, 27'. The channels 26, 26', 27, and 27' are optional features. Instead, the core may not have any channels or may have any number of channels.

These and other components of the example absorbent article will now be discussed in more details.

Topsheet

The topsheet 24 may be the part of the absorbent article that is in contact with the wearer's skin. The topsheet 24 may be joined to the backsheet 21, the core 28 and/or any other layers as is known to those of skill in the art. Usually, the topsheet 24 and the backsheet 21 are joined directly to each other in some locations (e.g., on or close to the periphery of the absorbent article) and are indirectly joined together in other locations by directly joining them to one or more other elements of the article 20.

The topsheet 24 may be compliant, soft-feeling, and non-irritating to the wearer's skin. Further, a portion of, or all of, the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art. A suitable topsheet comprising a web of spunbond polypropylene (topically treated with a hydrophilic surfactant) is manufactured by Polymer Group, Inc., of Charlotte, N.C., under the designation P-10.

Any portion of the topsheet 24 may be coated with a lotion and/or a skin care composition as is generally disclosed in the art. The topsheet 24 may also comprise or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of fluids therethrough. The size of at least the primary apertures is important in achieving the desired fluid encapsulation performance. If the primary apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased. Typically, the total area of the apertures at the surface of a diaper may have an area of between about 10 cm$^2$ and about 50 cm$^2$ or between about 15 cm$^2$ and 35 cm$^2$. Examples of apertured topsheets are disclosed in U.S. Pat. No. 6,632,504, assigned to BBA NONWOVENS SIMPSONVILLE. Typical diaper topsheets have a basis weight of from about 10 gsm to about 50 gsm or from about 12gsm to about 30 gsm, but other basis weights are within the scope of the present disclosure.

Backsheet

The film layer 25 of the backsheet 21 is generally the portion of the absorbent article 20 positioned adjacent to the garment-facing surface of the absorbent core 28 and prevents, or at least inhibits, the fluids and bodily exudates absorbed and contained therein from soiling articles such as bed sheets and undergarments. The film layer 25 is typically impermeable, or at least substantially impermeable, to fluids (e.g., urine). The film layer may be a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. In place of, or in addition to film materials as described above, the backsheet 21 may include a breathable material layer which permits vapors to escape from the absorbent article 20 while still preventing, or at least inhibiting, fluids from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The film layer 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the article 20.

The backsheet 21 also includes an outer cover layer 23 that overlaps at least a portion of, or the entire film layer 25, to form a soft garment-facing surface of the absorbent article. The outer cover layer 23 may be formed of one or more nonwoven materials. The outer cover layer 23 may be joined to at least a portion of the film layer 25 through mechanical bonding, adhesive bonding, or other suitable methods of attachment. The outer cover layer 23 may cover the entire film 25, wherein the outer cover may be joined to the film though application of backsheet adhesive in a first pattern between the two layers of the backsheet 21 (either through backsheet adhesive application on the film layer 25 or on the outer cover layer 23, or a combination of both). The first pattern of backsheet adhesive between the two layers of the backsheet may continue from the front waist edge 10 to the rear waist edge 12 (or any distance between the front waist edge 10 and the rear waist edge 12), and continue between the first side edge 3 and the second side edge 4 (or any distance between the first side edge 3 and the second side edge 4). The backsheet adhesive applied in a first pattern may be alternating adhesive stripes 29 and adhesive-free stripes 30. The first pattern of backsheet adhesive stripes may be a repeating pattern of: a 1.0 mm wide stripe of backsheet adhesive running in the longitudinal direction of the absorbent article, followed by a 1.0 mm wide stripe that is free of backsheet adhesive running in the longitudinal direction of the absorbent article (the repeating units repeating across the width direction W of the absorbent article). Alternatively, the first pattern of background adhesive stripes may be a repeating pattern of: a 1.0 mm wide stripe of backsheet adhesive running in the lateral direction of the absorbent article, followed by a 1.0 mm wide stripe that is free of backsheet adhesive running in the lateral direction of the absorbent article (the repeating units repeating across the length direction L of the absorbent article).

The above detailed first pattern of backsheet adhesive will provide about 50% adhesive coverage of the surface area of the garment facing surface of the film layer 25 (i.e., for every 1 mm width of backsheet adhesive, there is a 1 mm wide adhesive-free stripe on the garment facing surface of the film layer). Alternatively, the first pattern of backsheet adhesive may provide about 30%, about 40%, about 60%, about 70%, or about 80% adhesive coverage of the surface area of the garment facing surface of the film layer 25. The first pattern of backsheet adhesive that are stripes, the stripes (running either lengthwise or widthwise) may also be a pattern of: A) about a 1.0 mm wide stripe of backsheet adhesive, and about a 2.0 mm wide stripe that is free of backsheet adhesive; B) about a 2.0 mm wide stripe of backsheet adhesive, and about a 2.0 mm wide stripe that is free of backsheet adhesive; C) about a 2.0 mm wide stripe of backsheet adhesive, and about a 1.0 mm wide stripe that is free of backsheet adhesive; D) about a 0.5 mm wide stripe of backsheet adhesive, and about a 0.5 mm wide stripe that is free of backsheet adhesive; E) about a 0.5 mm wide stripe of backsheet adhesive, and about a 1.0 mm wide stripe that is free of backsheet adhesive; or F) about a 0.5 mm wide stripe of backsheet adhesive, and about a 2.0 mm wide stripe that is free of backsheet adhesive. The pattern may include a repeating unit (repeating lengthwise or widthwise) of backsheet adhesive applied in a stripe that is about 0.1 mm to about 4.0 mm wide, adjacent to a stripe that is backsheet adhesive free and is about 0.1 mm to about 4.0 mm wide, or a first pattern that includes any width of backsheet adhesive and/or sections that are backsheet adhesive free within those recited ranges. The stripes of backsheet adhesive may be applied at a basis weight of between about 1.0 g/m$^2$ and about 6.0 g/m$^2$, or between about 1.5 g/m$^2$ and about 5.0 g/m$^2$, or between about 1.8g/m$^2$ and about 4.0 g/m$^2$, or between about 2.0 g/m$^2$ and about 3.0 g/m$^2$, or about 2.5 g/m$^2$.

Figure 14:
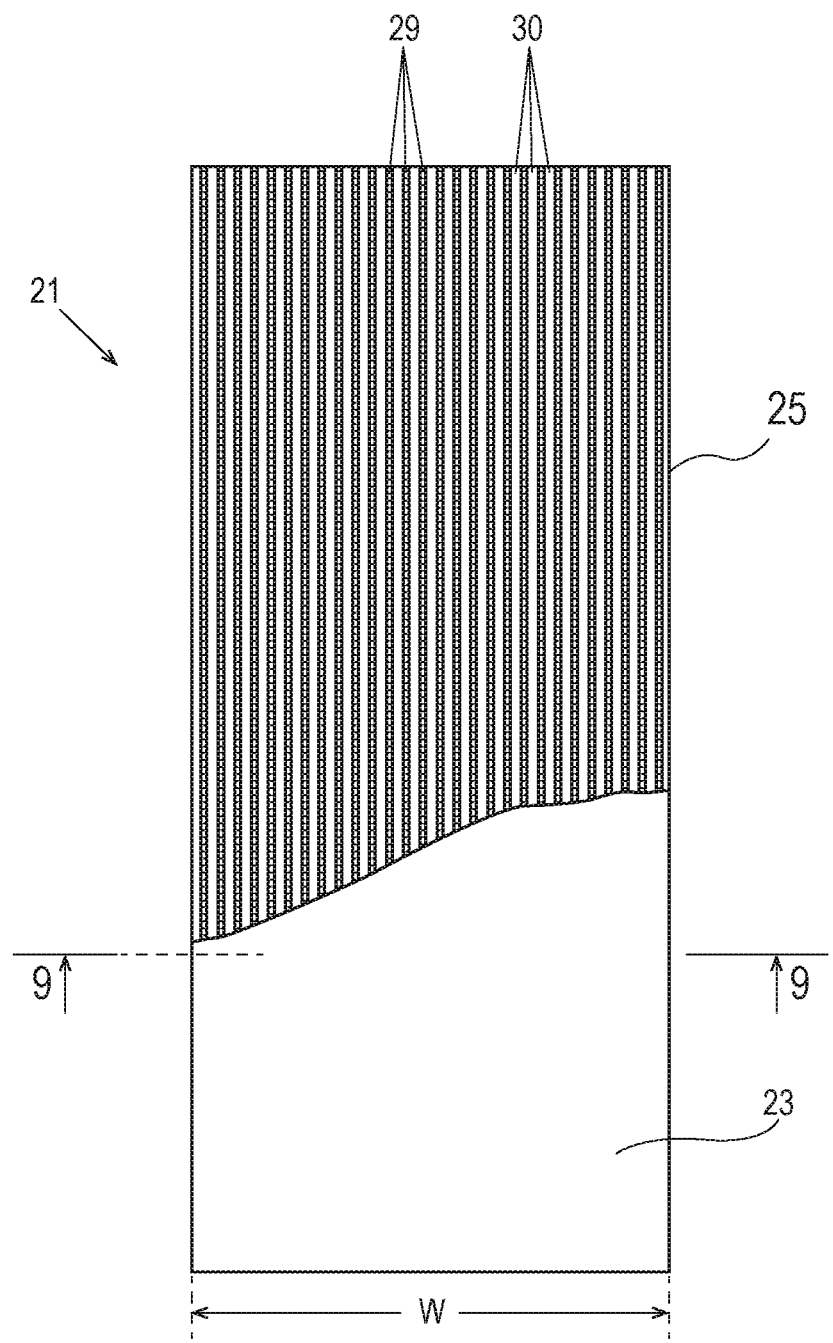
FIG. 14 is a top view of the backsheet of FIGS. 1-5.
Figure 15:
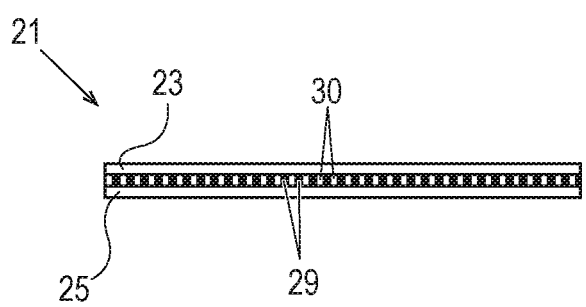
FIG. 15 is a cross sectional view of the backsheet of FIG. 14, taken through line 9-9.

FIG. 14 illustrates a top view of the backsheet 21 (as included in the absorbent articles 20 of FIGS. 1-5), comprising an outer cover layer 23 and a film layer 25, with a first pattern of backsheet adhesive stripes between the layers (and thus covering a percentage of the garment facing surface of the film layer). The outer cover layer 23 is shown cut away to detail a first pattern that includes backsheet adhesive stripes 29 and widths that are free of backsheet adhesive 30 (shown in a repeating pattern across the width W of the backsheet, with the stripes running in the longitudinal direction of the absorbent article) on the garment facing surface of the film layer 25. FIG. 15 shows a cross sectional view across line 9-9 of the backsheet 21, to again detail the first pattern of backsheet adhesive between the outer cover layer 23 and the film layer 25.

The outer cover 23 may have a bonding pattern covering the entire outer cover, or only covering a portion of the outer cover. For example, the outer cover 23 may have a bonding pattern covering the portion of the outer cover that is used as the female fastening material of the fastening system. Examples of bonding patterns that are useful on the outer cover 23 detailed herein are described in U.S. Patent Publication No. 2013/0253461 A1, filed on Mar. 23, 2012.

Bond Patterns for the Outer Cover Layer of the Backsheet

It is believed that the features of consolidating bond shapes and patterns described below may be particularly useful in applications of outer cover layers 23 of relatively low basis weights in some applications, in that it is believed that such features provide a way to enhance loft while reducing, or at least without adding, basis weight. Accordingly, for such applications, a nonwoven having a basis weight from 6.0 to 50 gsm, more preferably from 8.0 to 35 gsm, even more preferably from 9.0 to 25 gsm, and still more preferably from 10 to 20 gsm may be used.

Figure 9A:
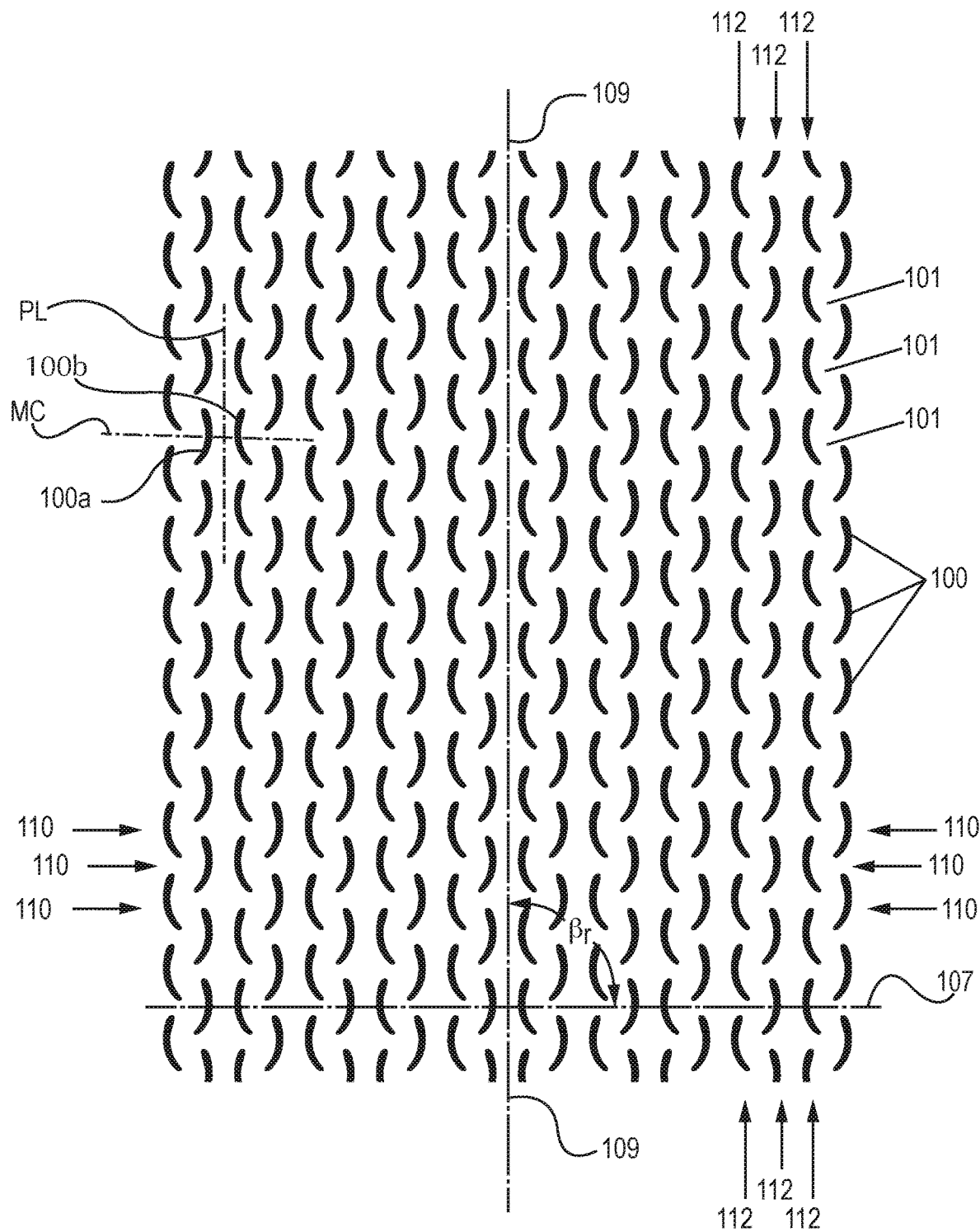
FIG. 9A is a view of a pattern of bonding surface shapes of bonding protrusions that may be imparted to the surface of a calender roller, to create another corresponding pattern of consolidating bond impressions having bond shapes in a nonwoven web.
Figure 9B:
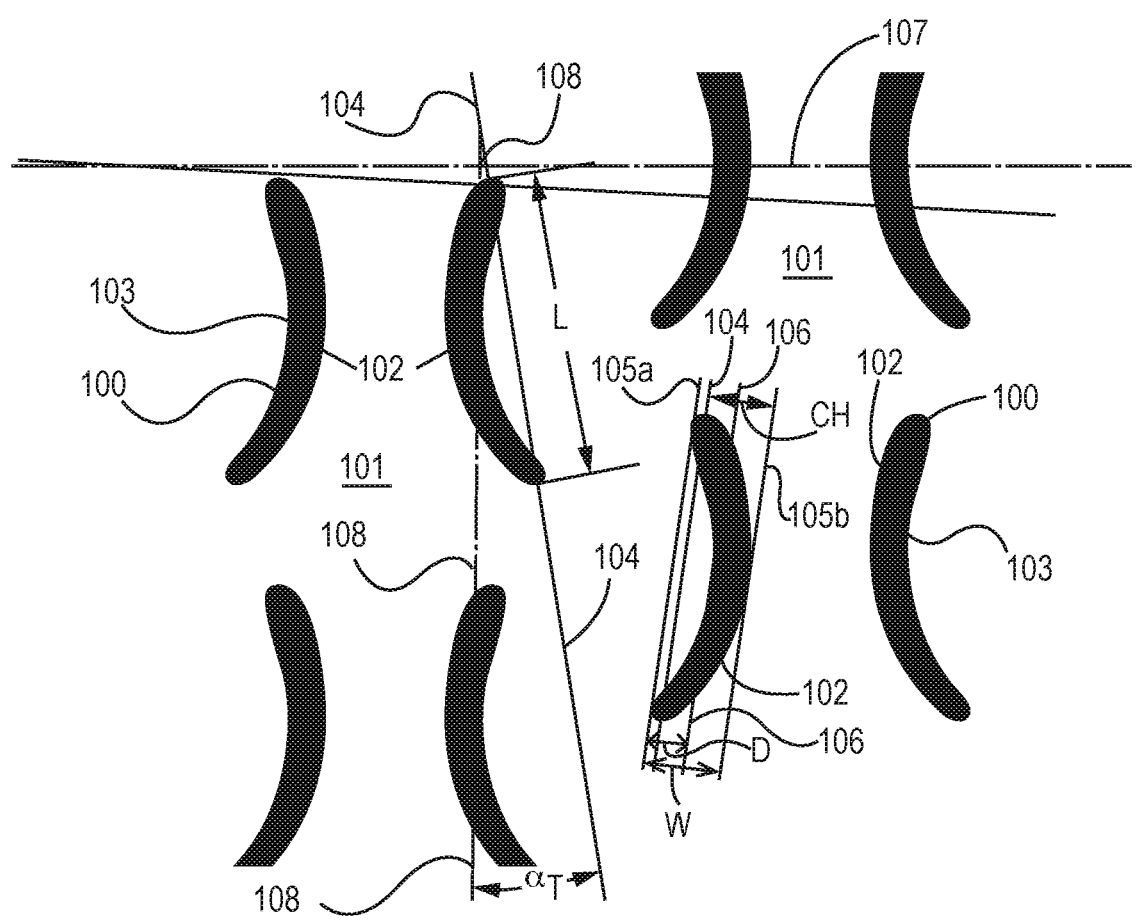
FIG. 9B is a magnified view of the pattern of bonding surface shapes of bonding protrusions or consolidating bond impressions having bond shapes appearing in FIG. 9A.
Figure 9C:
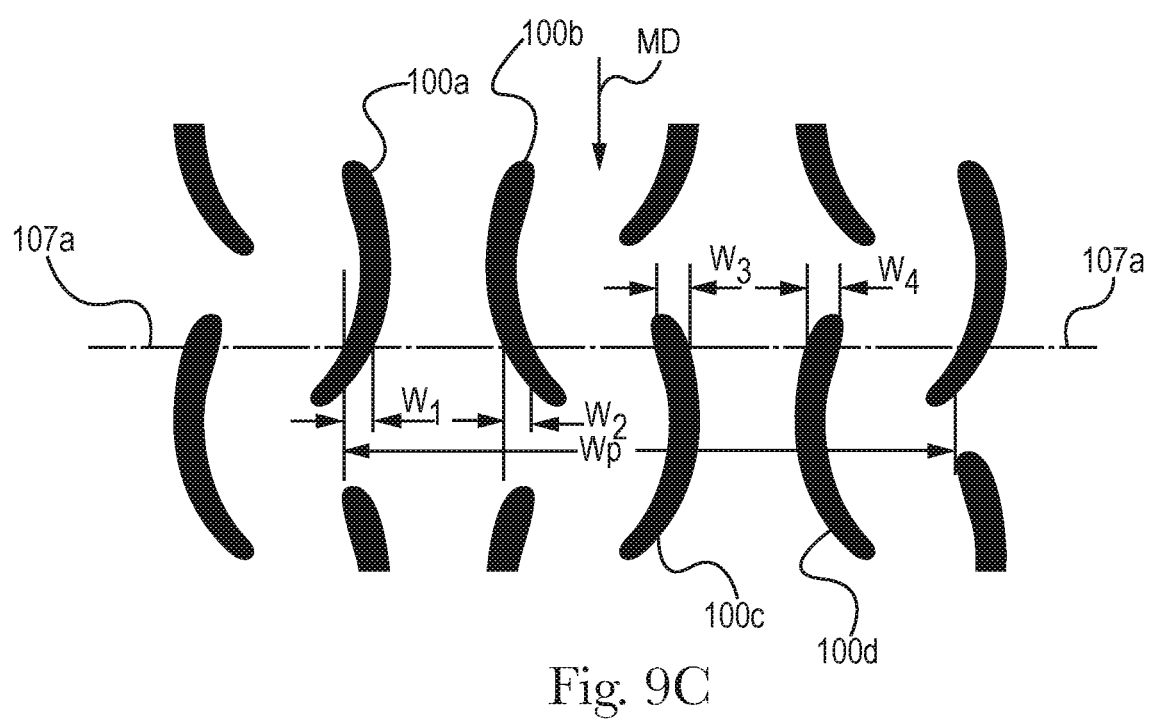
FIG. 9C is a magnified view of the pattern of bonding surface shapes of bonding protrusions or consolidating bond impressions having bonding impressions appearing in FIG. 9A.

FIGS. 9A, 9B and 9C depict one example of a bonding pattern and bonding shapes that will be reflected in bond shapes of bond impressions in a nonwoven web. Bonding shapes 100 represent the shapes of bonding surfaces of bonding protrusions that may be imparted to a bonding roller by etching, machining or other methods. Such bonding protrusions on a bonding roller will impress bond impressions into a web, of like bond shapes, arranged in a like bonding pattern. Without intending to be bound by theory, it is believed that certain aspects and features of the depicted shapes and pattern may have the beneficial effect described above.

Referring to FIG. 9B, the bonding shape 100 has a greatest measurable length L, which is measured by identifying a shape length line 104 intersecting the perimeter of the shape at points of intersection that are the greatest distance apart that may be identified on the perimeter, i.e., the distance between the two farthest-most points on the perimeter. The bonding shape 100 has a greatest measurable width W which is measured by identifying respective shape width lines 105a, 105b which are parallel to shape length line 104 and tangent to the shape perimeter at one or more outermost points that are most distant from shape length line 104 on either side of it, as reflected in FIG. 9B. It will be appreciated that, for some shapes (e.g., a semicircle), one of shape width lines 105a, 105b may be coincident/colinear with shape length line 104. Greatest measurable width W is the distance between shape width lines 105a, 105b. Shapes within the scope of the present invention have an aspect ratio of greatest measurable length L to greatest measurable width W of at least 2.5, more preferably at least 2.7, and even more preferably at least 2.8. The bond shapes and sizes impressed on the nonwoven web will reflect and correspond with the bonding shapes 100 and sizes thereof on the roller.

Still referring to FIG. 9B, a bonding shape 100 may have a shape perimeter with a convex portion 102, lying on one side of the shape length line 104. FIG. 9B shows also that the convex portion may have a varying radius or radii. The varying radius/radii of the convex portion 102 may render the shape perimeter similar to the profile of the camber of an airfoil in cross section. Viewed another way, the cross-sectional profile of an airfoil has a convex portion and is asymmetric about any line or axis that traverses the profile, which can be identified. The convex portion 102 may have a camber height CH measured as the distance between shape length line 104 and the shape width line 105b that is tangent to the convex portion 102. It is believed that, for maximum beneficial impact on airflow, it may be desirable that the ratio between camber height CH and greatest measurable length L be 0.30 or less, more preferably 0.25 or less, but greater than zero. It is believed that a bonding protrusion having a cross section along a plane parallel the bonding surface, fitting this description, repeated and arranged in a pattern, has beneficial effects on acceleration and deceleration of air through nonwoven fibers at and about the nip. Again, the bond shapes and sizes impressed on the nonwoven web will reflect and correspond with the bonding shapes and sizes on the roller.

The shape perimeter may have a convex portion with or without a varying radius on both sides of shape length line 104, such that it has the overall contour of an airfoil with symmetrical camber, in cross section. In another alternative, the shape perimeter may have a convex portion on one side of shape length line 104 and a straight portion on or on the other side of shape length line 104, such that it has the overall contour of an airfoil/aircraft wing with asymmetrical camber, in cross section. In another alternative, the shape perimeter may have a convex portion on one side of shape length line 104 and a concave portion 103 disposed substantially opposite the concave portion, as reflected in FIG. 9B, such that it has the overall contour of an airfoil/aircraft wing with asymmetrical camber and relatively high-loft, low-speed features, in cross section.

The extent of the concavity of concave portion 103 may be quantified by measuring the depth thereof, relative the greatest measurable length. The concavity depth D may be measured by identifying a shape concavity line 106 that is parallel with the shape length line 104 and tangent to the deepest point along the concave portion 103. The concavity depth D is the distance between the shape width line 105a facing the concavity and the shape concavity line 106. The extent of the concavity of concave portion 103 may be expressed as a ratio of concavity depth D to shape length L (hereinafter, "concavity depth ratio"). Although shapes that do not have a concave portion 103 are contemplated, it may be desirable that a bonding shape has a concave portion having a concavity depth ratio between 0.00 and 0.30, more preferably between 0.00 and 0.25, and even more preferably between 0.00 and 0.20. Again, the bond shapes and sizes impressed on the nonwoven web will reflect and correspond with the bonding shapes and sizes on the roller.

Whilst the explanation above refers to bonding protrusions and resulting consolidated bond shapes in the web, which have bonding shape/bond shape perimeters following "convex" and/or "concave" (impliedly, smooth) curves, it may be appreciated that the effect may be substantially realized by approximating such smooth curves with chains of straight line segments. Accordingly, each of the terms "convex" and "concave" herein includes a portion of a shape perimeter formed of a chain of 5 or more straight line segments lying on one side of a shape length line and connected end-to-end, that is each a chord of a smooth convex or concave curve lying on one side of the shape length line, or portion of a curve lying on one side of the shape length line that does not include an inflection point.

Without intending to be bound by theory, it is believed that calender roller bonding protrusions having bonding shapes with one or more features as described above have aerodynamic effects on air flow in and about the nip, that cause acceleration and deceleration of air in and about the interstices of the nonwoven fibers in a way that repositions the fibers, and may affect teasing or fluffing, adding loft and caliper.

Additionally, the rotational orientations of the protrusions affect the orientations of the bonding protrusions at the nip, and it is believed that this has an impact. Bonding shapes 100 and the bonding protrusions supporting them may be arranged along an individual shape tilt angle relative the machine and cross directions. Without intending to be bound by theory, it is believed that the shape tilt angle should not exceed a certain amount for the bonding protrusion to have maximum beneficial effect on air flow. Referring again to FIG. 9B, the shape tilt angle $\alpha_T$ may be expressed as the smaller angle formed by the intersection of an axis along the machine direction 108 and the shape length line 104. It is believed, that the shape and the shape tilt angle have cooperating effects on the air flow. In the case of an asymmetric bonding shape, such as the described airfoil-like shape, it is believed that this asymmetric bonding shape is sufficient for effecting the desired changes in air flow. However, a rotational orientation with a tilt angle of more than zero may enhance the effect. With respect to a bonding shape that is not asymmetric, it is believed that the shape tilt angle $\alpha_T$ provides the desired effects on air flow, such that it then should not be less than 1 degree and should not exceed 40 degrees, more preferably, 30 degrees, and still more preferably, 20 degrees. It is believed that a shape tilt angle within this range effectively provides air flow through the nip, while at the same time, imparts cross-direction vector components to air flows through the nip. Conversely, a shape tilt angle greater than 40 degrees may create too much of an obstruction to air flow through the nip to have a beneficial effect, and even greater shape tilt angles combined with sufficient density of bonding protrusions may have the effect of creating enough obstruction at the nip to substantially divert airflow from the nip, i.e. , toward the sides of the bonding rollers, rather than through the nip. The bond shapes and rotational orientations impressed on the nonwoven web will reflect and correspond with the bonding shapes and rotational orientations on the roller.

It is believed that air flows having cross-direction vector components flowing across or through the batt/web as it passes through and exits the nip may urge fibers in the cross-direction, helping add loft, caliper and/or cross direction tensile strength. It will be appreciated that the fibers of many nonwoven bates are laid down in the nonwoven web manufacturing process with a general machine direction orientation or bias, which tends to result in the finished web having relatively greater machine direction tensile strength, and relatively less cross direction tensile strength. Thus, any process that tends to impart some added cross-direction orientation to the fibers prior to bonding may be useful for increasing cross direction tensile strength, bringing about better balance between machine direction tensile strength and cross-direction tensile strength, and adding loft such as by repositioning of the fibers in the z-direction. It is believed that, for best results, it may be even more desirable that shape tilt angle $\alpha_T$ is between 5 degrees and 15 degrees, more preferably between 8 degrees and 12 degrees, and even more preferably between 9 degrees and 11 degrees, for the most beneficial effects on airflow at the line speeds contemplated herein. The rotational orientation of the bonding pattern impressed on the nonwoven web will reflect and correspond with the rotational orientation of the bonding pattern on the roller.

As suggested above, in order to gain the benefit of energy from a substantial mass of air flowing through the nip, it is also believed desirable that a pattern of bonding protrusions not be excessively obstructive of air flow through the nip, nor that it remove too much energy from the air flow by overly slowing, or halting, and absorbing the energy from, forward (machine-direction) momentum of air flows. Referring to FIG. 9C, a nip line 107a along the cross direction is identified along a pattern where the bonding shapes occupy the greatest proportion of distance along a cross direction line that can be identified in a pattern. Thus, nip line 107a located as shown represents a cross-direction line along which bonding protrusions presented the greatest amount of obstruction that can be identified in a particular pattern, to air flow through the nip, during the bonding process. A repeating series of shapes can be identified; in this example, the repeating series consists of the four shapes 100a, 100b, 100c and 100d. Widths $w_1$, $w_2$, $w_3$, and $w_4$ of the identified shapes 100a, 100b, 100c, 100d in the repeating series reflect restriction of air flow along the nip line 107a. Width $w_p$ is the width of the entire repeating series, including the distances between the bonding shapes. The proportion of maximum restriction along the nip length for the pattern is reflected by the ratio $(w_1+w_2+w_3+w_4 \ldots +w_n)/w_p$, referred to herein as the nip airflow restriction ratio (where "w" is the cross-direction width along the nip line 107a of a bonding shape perimeter, and "n" is the number of bonding shapes along nip line 107a that make up a repeating series). In order that a bonding pattern allows for effective air flow through the nip in order to take advantage of energy of moving air, it may be desirable that the nip airflow restriction ratio be 0.40 or less, more preferably 0.30 or less, and even more preferably 0.25 or less. The bond shapes, rotational orientations and density/numerosity per unit surface area of bond impressions on the nonwoven web will reflect and correspond with the bonding shapes, rotational orientations and density/numerosity per unit surface area of bonding protrusions on the roller, and thus, also reflect the airflow restriction ratio.

Figure 10A:
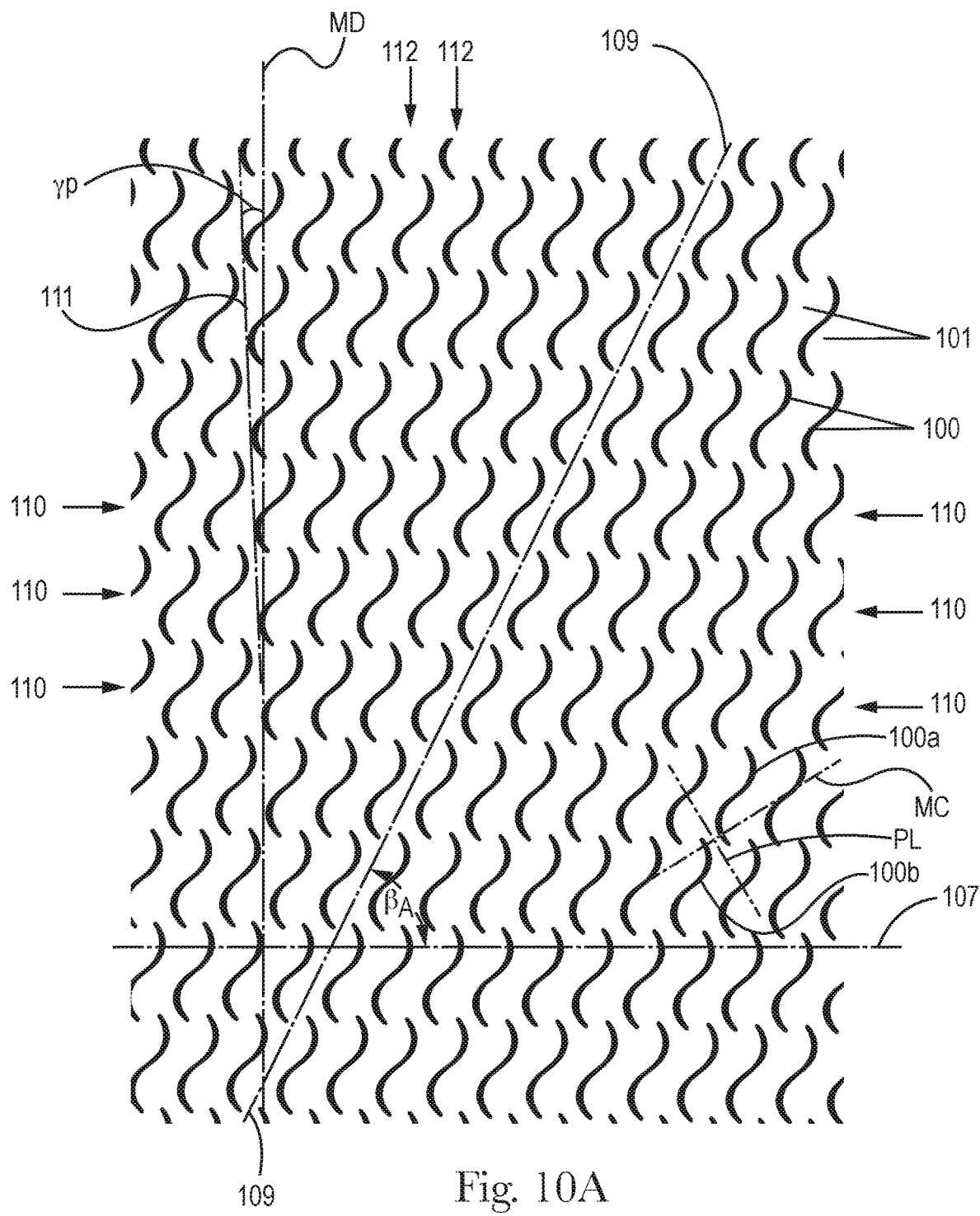
FIG. 10A is a view of another pattern of bonding imparted to the surface of nonwoven created by another corresponding pattern of consolidating bond protrusions on a calendar roller surface.
Figure 10B:
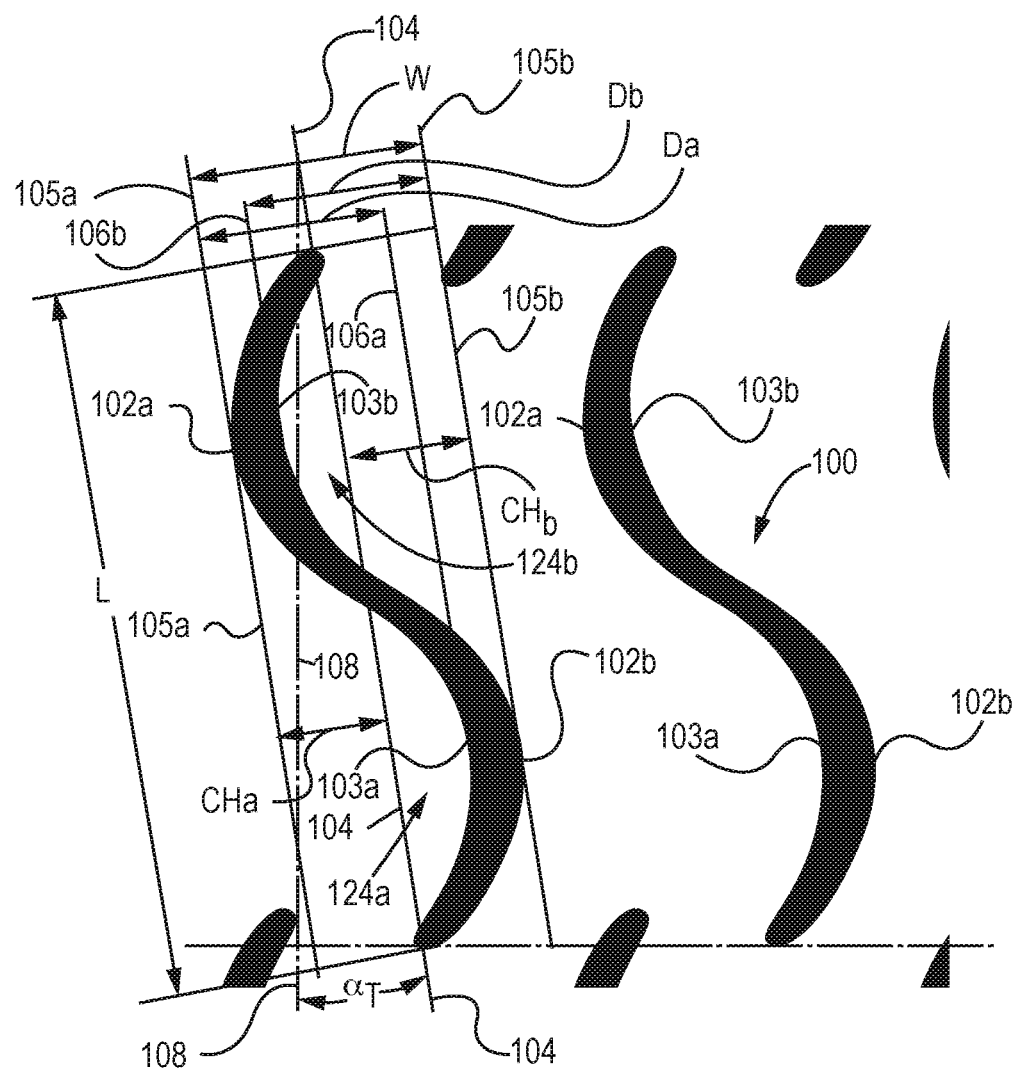
FIG. 10B is a magnified view of the pattern of bonding surface shapes of bonding protrusions or consolidating bond impressions on a calendar roller surface having bond shapes appearing in FIG. 10A.

Referring to FIGS. 10A and 10B, an alternative bonding pattern is depicted. The repeated bonding shape 100 and profile of the associated bonding protrusion is a composite of two generally convex/concave sub-shapes joined or superimposed at their respective tips, in reversed orientation, to form an open "S" shape which is rotationally symmetric about this juncture of the component sub-shapes, respectively its middle inflection point. It will be appreciated, however, that the depicted repeated "S" shape may have several of the features of the bonding shape depicted in FIGS. 9A and 9B, described above, which are believed to be beneficial. The depicted bonding shape 100 in FIGS. 10A and 10B has a greatest measurable length L and greatest measurable width W, measured with respect to shape length line 104 and shape width lines 105a, 105b, identified in the manner described above. As set forth above, bonding shapes 100 within the scope of the present invention have an aspect ratio of greatest measurable length L to greatest measurable width W of at least 2.5, more preferably at least 2.7, and even more preferably at least 2.8.

The depicted bonding shape in FIGS. 10A and 10B also has convex portions 102a, 102b along its perimeter. One or both of the convex portions 102a, 102b may have varying radii, and have camber heights CHA and CHB. It is believed that, for maximum beneficial impact on airflow, it may be desirable that the ratio between camber height CH and the greatest measurable length L also be 0.30 or less, more preferably 0.25 or less, but greater than zero.

The depicted bonding shape also has concave portions 103a and 103b along its perimeter. Concavity depth Da is the distance between shape width line 105a facing concavity 103a, and shape concavity line 106a. Concavity depth Db is the distance between shape width line 105b facing concavity 103b, and shape concavity line 106b. Although bonding shapes that do not have a concave portion 103a, 103b along their perimeters are contemplated, it may be desirable that a bonding shape perimeter has one or more concave portions such as concave portions 103a, 103b having a concavity depth ratio:

Concavity depth/(L*nc)≤0.30, more preferably 0.25, and even more preferably 0.20, where nc is the number of fully enclosed shapes that are defined by portions of the bonding shape perimeter and the shape length line, which evidence concavities. For example, for the "S" shape shown in FIG. 10B, nc =2 because there are 2 such fully enclosed shapes 124a and 124b.

The shapes 100 in FIGS. 10A and 10B also may have a shape tilt angle $\alpha_T$ determined as set forth above, and within the ranges set forth. The geometric features of the bond shapes and pattern on the nonwoven web will reflect and correspond with those of the shape, size, rotational orientation, density and arrangement of the bond shapes 100.

It is also believed that arranging the bonding protrusions in a pattern such that a relatively straight, unobstructed passageway between them exists along recessed areas 101 at the nip, at least partially along the machine direction, may have beneficial effects. Referring to FIGS. 9A and 10A, it can be seen that each example has a cross-nip airflow line 109 that can be identified, that intersects no bonding shape, and intersects a cross direction axis 107 at an angle such that it has a machine direction vector component. Cross-nip airflow line 109 intersects cross direction axis 107 to form a smaller angle, identified herein as cross-nip airflow angle $\beta_A$. It is believed that cross-nip airflow angle $\beta_A$ is preferably greater than 45 degrees, more preferably between 50 degrees and 90 degrees, and even more preferably between 60 degrees and 90 degrees. It is believed desirable that cross-nip airflow line 109 should extend indefinitely without intersecting a bonding shape 100, but at a minimum, past at least 8 rows 110 of bonding shapes 100 without intersecting a bond shape. Again, geometric features of the bond shapes and pattern on the nonwoven web will reflect and correspond with those of the shape, size, rotational orientation, density and arrangement of the bond shapes 100.

Another aspect of the bonding shapes and patterns depicted in, e.g., FIGS. 9A-10B is that they may have any combination of the above-described aspect ratios, maximum nip airflow restriction ratio (0.40 or less), shape asymmetry, shape tilt angles, and other features, and may also reflect use of adjacent pairs of bonding protrusions that define air passageways through the nip that alternately narrow and widen, or converge and diverge, in the manner of a venturi. For example, referring again to FIGS. 9A and 10A, two adjacent bond shapes 100a, 100b may be identified. Herein, "adjacent" means that at least portions of the perimeters of a pair of shapes face each other with no intervening shapes between them; and that the pair of shapes has machine-direction overlap. The pair of shapes has machine-direction overlap if one or more cross-direction lines 107 that are tangent to and/or cross the perimeters of each of the shapes may be identified. A minimum passageway clearance line MC may be identified connecting the perimeters of the shapes 100a, 100b, at the location where the shortest measurable distance between the perimeters exists. The minimum passageway clearance line MC will necessarily meet the perimeter of each of the adjacent shapes where line MC is normal to the perimeter, and line MC identifies the point of greatest constriction of an air passageway between the shapes (i.e., through the corresponding bonding protrusions) proximate and through the nip. A passageway line PL may be identified, perpendicular to the minimum passageway clearance line MC and lying between the adjacent shapes 100a, 100b.

The minimum passageway clearance line MC crosses and identifies a "venturi passageway" if the perimeter of each of the adjacent shapes 100a, 100b diverges away from the passageway line PL moving along the perimeter away from the minimum clearance line MC in both directions. It can be seen in FIGS. 9A and 10A that adjacent shapes 100a, 100b embody this feature.

Without intending to be bound by theory, it is believed that such venturi passageways have the effect of causing localized zones of acceleration and deceleration, and increases and decreases in pressure, as well as turbulence, of air as it passes through the nip. It is believed that these effects serve to tease and/or fluff the fibers of the batt and web about the nip.

For purposes of downstream handling and manufacturing processes, it may be desirable to ensure that no line along the machine direction exists along the nonwoven web surface that is indefinitely long without intersecting a bond impression. This condition (indefinitely long machine direction strip of web without bonds) may result in relatively long lengths of unbonded fibers that may be prone to moving away from a cutting knife in downstream machine direction web slitting operations, resulting in a poorly defined or sloppy slit edge. Additionally, such long, unbonded fibers may also separate from a manufactured edge or slit edge of the web (fraying), which may cause other difficulties in downstream operations. To avoid this condition, it may be desirable to impart a pattern angle $\gamma_P$ to the bonding pattern. Referring to FIGS. 10A, pattern angle $\gamma_P$ may be expressed as the smaller angle formed by the intersection of a line 111 connecting like points on repeating, similarly oriented shapes in columns 112, and a machine direction axis. To avoid the above-mentioned problems, it may be desirable that pattern angle $\gamma_P$ be greater than 0 degrees. A pattern angle greater than 0 degrees will ensure that an indefinitely long machine direction strip of web without bonds will not exist. To avoid creating complications with respect to the air flow benefits of the pattern, however, it may be desirable to limit pattern angle $\gamma_P$ to 4 degrees or less, more preferably 3 degrees or less, and even more preferably 2.5 degrees or less. Again, features of the bond pattern on the nonwoven web including pattern angle will reflect and correspond with those of the pattern and pattern angle $\gamma_P$ on the roller.

An additional aspect that it believed important is bonding area of a roller, reflected in bond area on the web. Imagining a pattern of bonding surfaces having shapes reflected in FIGS. 9A and 10A impressed on a surface of a nonwoven web, bonding area and bond area is the area occupied by the bonding shapes on the roller and bond shapes impressed on the surface of the web. In the field of nonwoven web manufacturing, bonding area is often expressed as a percentage, calculated as:

$$\text{Bonding Area \%} = \left[ \frac{\text{(bonding area within a surface area unit)}}{\text{(total surface area of the surface area unit)}} \right] \times 100\%$$

The bonding area reflects the combination of bonding protrusion density (number of bonding protrusions per unit surface area) and average surface area of the bonding shapes 100 in the unit surface area. Thus, increasing the number of bonding protrusions and/or increasing the surface area of the individual bond shapes 100 increases the bonding area, and vice versa. It is believed that bonding area has an impact on the entrainment of air as well as the proportion of entrained air carried toward the nip, which will pass through the nip. If bonding area is relatively greater, this means that more and/or larger bonding protrusions are present at the nip point at any time to obstruct air flow through the nip; conversely, if bonding area is relatively less, this means that fewer and/or smaller bonding protrusions are present at the nip point at any time to obstruct air flow through the nip. Bond area has another effect as well. Increasing bond area increases the number and proportion of the fibers in the nonwoven web that are bonded together, and vice versa. Within a certain range of bond area, tensile strength of the nonwoven web in the machine and/or cross directions may be increased by increasing the bond area. However, bending stiffness of the nonwoven web may be correspondingly increased, and loft decreased—compromising the soft feel and/or appearance of the nonwoven. In order to best realize the benefits of air flow, air compression and channeling believed to be occurring through use of the bond shapes described herein, enhancing loft, while still imparting satisfactory tensile properties to the web, it is believed that bonding area should be in the range of 4.0% and 18%, more preferably between 6% and 16%, and even more preferably between about 8% and 14%. At the line speeds contemplated herein, and relative to the bonding area, the average surface area per bonding shape affects bonding area and bonding protrusion density. It is believed desirable that the average bonding shape 100 surface area be in the range of 0.3 mm$^2$ and 10 mm$^2$. Correspondingly, it is believed desirable that the density of the bonding protrusions, and correspondingly, the impressed bond shapes, be between 0.4 bonding protrusions/cm$^2$ for bonding shape/bond shape area of 10 mm$^2$ at 4% bonding area and 60 bonding protrusions/cm$^2$ for bonding shape/bond shape area of 0.3 mm$^2$ at 18% bonding area Similar calculations of bonding protrusion density and average bond shape surface area to arrive at the bond areas in the ranges set forth above, will be appreciated. The surface area and density of bond shapes impressed on the nonwoven web will reflect and correspond with those of the bonding shapes, and thus, the bond area on the web will reflect and correspond with the bonding area on the roller as well.

It is believed that surface features of a bonding roller including the bonding protrusions affect the above detailed air flows. Particularly at the nip, the profiles of bonding protrusions present obstructions to airflow, while the recessed areas between the bonding protrusions present passageways. Thus, it is believed that for certain configurations, shapes, and positions of bonding protrusions, as will be reflected in the bond impressions created in the web, rotational orientation(s) and repeating patterns of the bonding shapes can be selected and formed to have a beneficial effect on these air flows. It is believed, further, that patterns of bonding protrusions having bonding surface shapes with certain features, reflected in the bonding surfaces and the cross sections of the protrusions along planes substantially parallel with the bonding surfaces, rotational orientations relative the plane approximated by the web surface, and spacing, may be employed to channel these air flows in a way that causes them to reposition the fibers during the calender bonding process, such as by teasing or fluffing the fibers, thus providing an enhanced calender-bonded nonwoven web having greater loft/caliper than a similar nonwoven web having other consolidated bond shapes and patterns, all other variables being the same.

Absorbent Core

As used herein, the term "absorbent core" refers to the component of the absorbent article having the most absorbent capacity and comprising an absorbent material and a core wrap or core bag enclosing the absorbent material. The term "absorbent core" does not include the acquisition and/or distribution system or any other components of the article which are not either integral part of the core wrap or core bag or placed within the core wrap or core bag. The absorbent core may comprise, consist essentially of, or consist of, a core wrap, an absorbent material (e.g., superabsorbent polymers) as discussed, and glue.

The absorbent core 28 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The core may also contain airfelt or cellulosic fibers with or without SAP.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This provides a relatively thin core compared to a conventional core typically comprising between 40-60% SAP and high content of cellulose fibers. The conventional cores are also within the scope of the present disclosure. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

Figure 4:
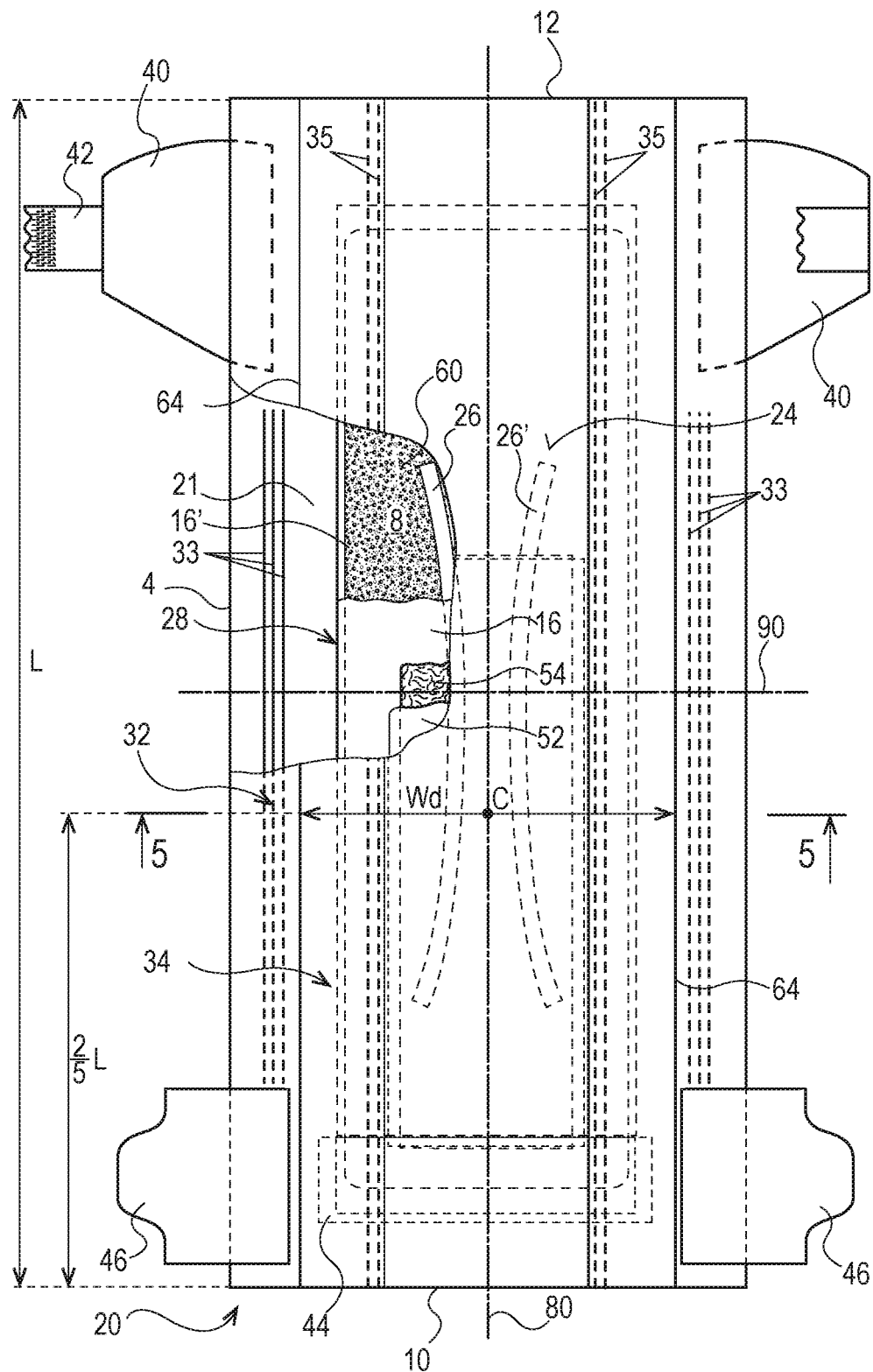
FIG. 4 is a top view of another absorbent article, wearer-facing surface facing the viewer, with some layers partially removed in accordance with the present disclosure.
Figure 5:
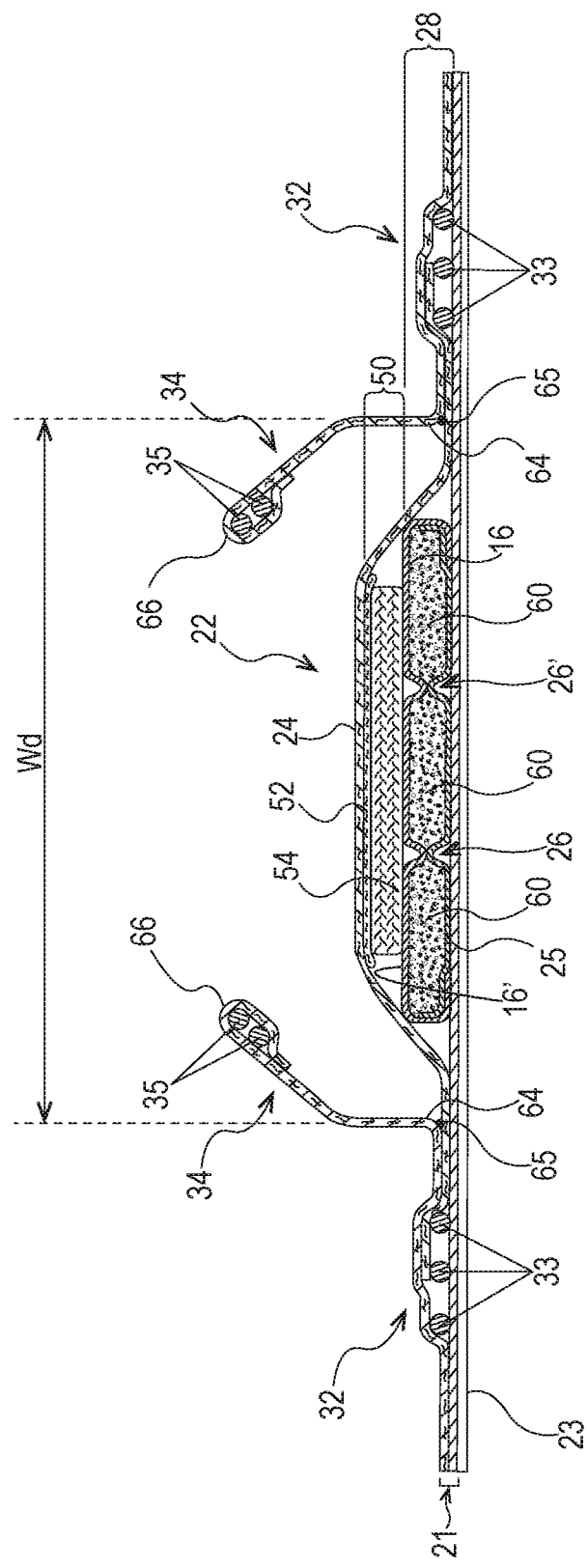
FIG. 5 is a cross-sectional view of the absorbent article taken about line 5-5 of FIG. 4 in accordance with the present disclosure.
Figure 6:
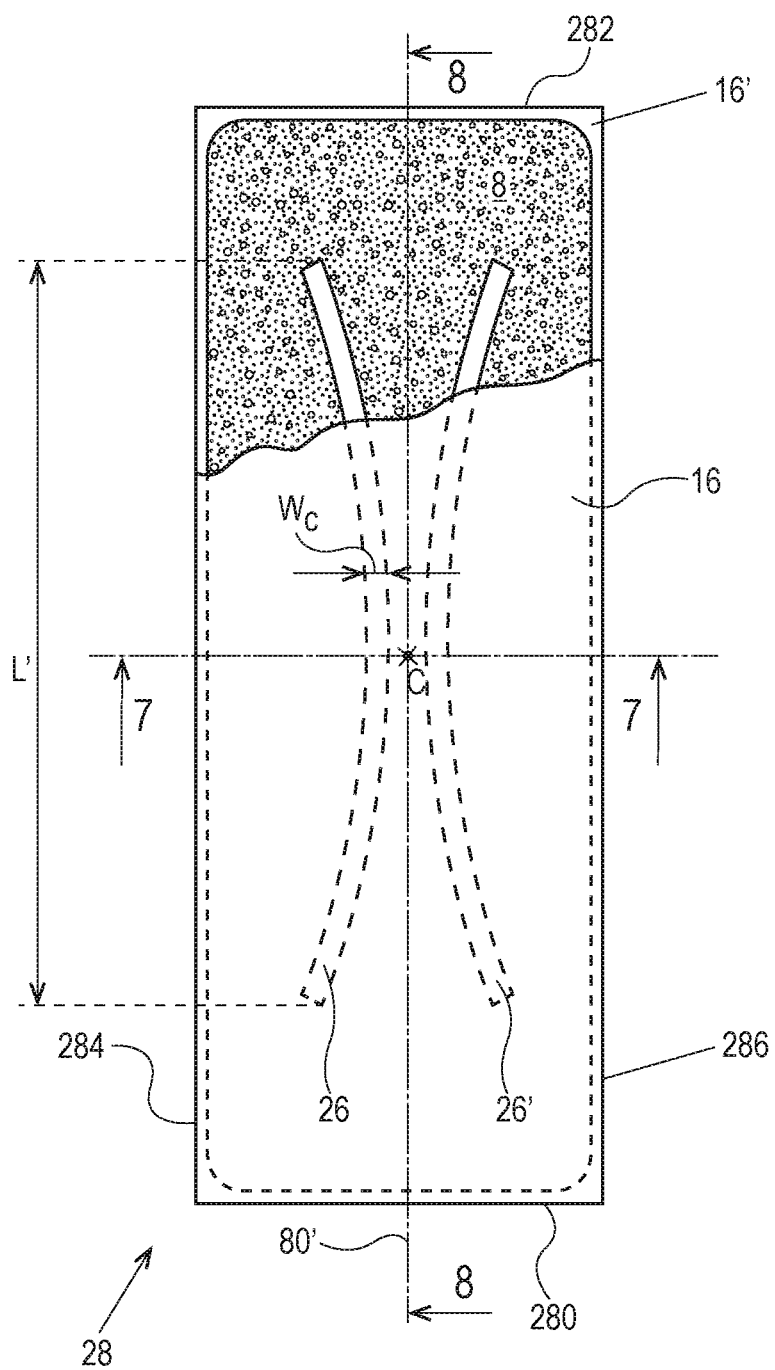
FIG. 6 is a top view of an absorbent core of the absorbent article of FIG. 4 with some layers partially removed in accordance the present disclosure.
Figure 7:
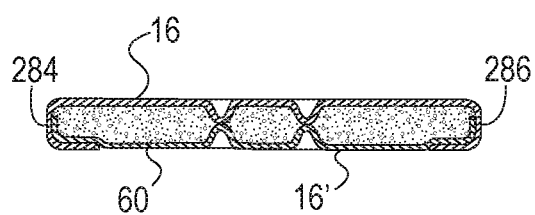
FIG. 7 is a cross-sectional view of the absorbent core taken about line 7-7 of FIG. 6 in accordance with the present disclosure.
Figure 8:
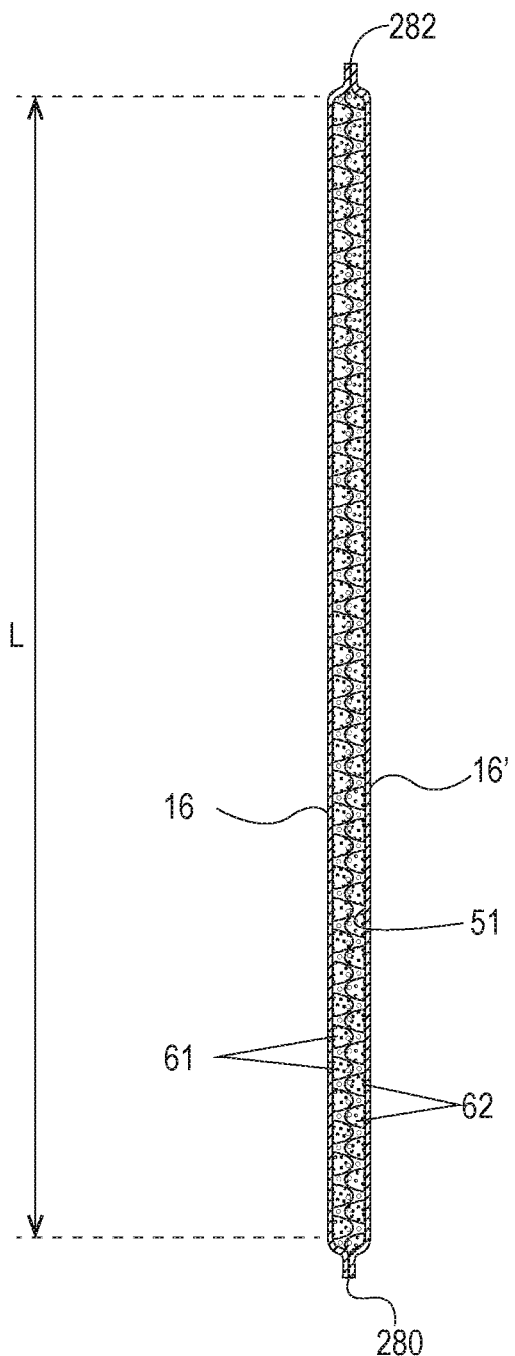
FIG. 8 is a cross-sectional view of the absorbent core taken about line 8-8 of FIG. 6 in accordance with the present disclosure.

The example absorbent core 28 of the absorbent article 20 of FIGS. 4-5 is shown in isolation in FIGS. 6-8. The absorbent core 28 may comprises a front side 280, a rear side 282, and two longitudinal sides 284, 286 joining the front side 280 and the rear side 282. The absorbent core 28 may also comprise a generally planar top side and a generally planar bottom side. The front side 280 of the core is the side of the core intended to be placed towards the front waist edge 10 of the absorbent article. The core 28 may have a longitudinal axis 80' corresponding substantially to the longitudinal axis 80 of the absorbent article 20, as seen from the top in a planar view as in FIG. 1. The absorbent material may be distributed in higher amount towards the front side 280 than towards the rear side 282 as more absorbency may be required at the front in particular absorbent articles. The front and rear sides 280 and 282 of the core may be shorter than the longitudinal sides 284 and 286 of the core. The core wrap may be formed by two nonwoven materials, substrates, laminates, or other materials, 16, 16' which may be at least partially sealed along the sides 284, 286 of the absorbent core 28. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H. B. Fuller, for example. The core wrap may extend to a larger area than strictly needed for containing the absorbent material within.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell. Elastomeric, hot-melt adhesives of these types are described in more detail in U.S. Pat. No. 4,731,066 issued to Korpman on Mar. 15, 1988. The thermoplastic adhesive material may be applied as fibers.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05 E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 10 or rear waist edge 12 may therefore may comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more g/m$^2$. The areas of the channels (e.g., 26, 26', 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 16, 16', four seals may be used to enclose the absorbent material 60 within the core wrap. For example, a first substrate 16 may be placed on one side of the core (the top side as represented in the Figures) and extend around the core's longitudinal edges to at least partially wrap the opposed bottom side of the core. The second substrate 16' may be present between the wrapped flaps of the first substrate 16 and the absorbent material 60. The flaps of the first substrate 16 may be glued to the second substrate 16' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, for example as shown in FIGS. 4-6, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 8 may comprise at least one channel 26, which is at least partially oriented in the longitudinal direction of the article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may have a length L' projected on the longitudinal axis 80 of the article that is at least 10% of the length L of the article. The channels may be formed in various ways. For example, the channels may be formed by zones within the absorbent material deposition area 8 which may be substantially free of, or free of, absorbent material, in particular SAP. In addition or alternatively, the channel(s) may also be formed by continuously or discontinuously bonding the top side of the core wrap to the bottom side of the core wrap through the absorbent material deposition area 8. The channels may be continuous but it is also envisioned that the channels may be intermittent. The acquisition-distribution system or layer 50, or another layer of the article, may also comprise channels, which may or not correspond to the channels of the absorbent core.

In some instances, the channels may be present at least at the same longitudinal level as the crotch point C or the lateral axis 60 in the absorbent article, as represented in FIG. 1 with the two longitudinally extending channels 26, 26'. The channels may also extend from the crotch region 7 or may be present in the front waist region 5 and/or in the rear waist region 6 of the article.

The absorbent core 28 may also comprise more than two channels, for example, at least 3, at least 4, at least 5, or at least 6 or more. Shorter channels may also be present, for example in the rear waist region 6 or the front waist region 5 of the core as represented by the pair of channels 27, 27' in FIG. 1 towards the front of the article. The channels may comprise one or more pairs of channels symmetrically arranged, or otherwise arranged relative to the longitudinal axis 80.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 8, and may therefore be fully encompassed within the absorbent material deposition area 8 of the core. The smallest distance between a channel and the closest edge of the absorbent material deposition area 8 may be at least 5 mm.

The channels may have a width We along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 8, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 34. Each barrier leg cuff may be formed by a piece of material which is bonded to the article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present at the level of the crotch point (C) or crotch region. The barrier leg cuffs may be joined at the proximal edge 64 with the chassis of the article by a bond 65 which may be made by gluing, fusion bonding, or a combination of other suitable bonding processes. The bond 65 at the proximal edge 64 may be continuous or intermittent. The bond 65 closest to the raised section of the leg cuffs delimits the proximal edge 64 of the standing up section of the leg cuffs.

The barrier leg cuffs may be integral with the topsheet 24 or the backsheet 25 or may be a separate material joined to the article's chassis. Each barrier leg cuff 34 may comprise one, two or more elastic strings 35 close to the free terminal edge 66 to provide a better seal.

In addition to the barrier leg cuffs 34, the article may comprise gasketing cuffs 32, which are joined to the chassis of the absorbent article, in particular to the topsheet 24 and/or the backsheet 25 and are placed externally relative to the barrier leg cuffs. The gasketing cuffs 32 may provide a better seal around the thighs of the wearer. Each gasketing leg cuff may comprise one or more elastic strings or elastic elements 33 in the chassis of the absorbent article between the topsheet 24 and backsheet 25 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 50 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 54 and an acquisition layer 52 disposed between the absorbent core and the topsheet, but the present disclosure is not so limited.

The ADS may comprise SAP as this may slow the acquisition and distribution of the fluids. Suitable ADS are described in WO 2000/59430 (Daley), WO 95/10996 (Richards), U.S. Pat. No. 5,700,254 (McDowall), and WO 02/067809 (Graef), for example.

In one example, the ADS may not be provided, or only one layer of the ADS may be provided, such as the distribution layer only or the acquisition layer only. When one of the three-dimensional, liquid permeable substrates of the present disclosure is used as a portion of, or all of, a topsheet, or positioned on a topsheet, dryness performance of the liquid permeable substrates may be improved if only one or no layers of the ADS are present. This is owing to the fact that fluids (e.g., urine) are easily able to wick through the liquid permeable substrates directly into the absorbent core 28 and/or into a one layer ADS.

Distribution Layer

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In still another example, the layer may comprise about 68% by weight chemically cross-linked cellulose fibers, about 16% by weight untreated pulp fibers, and about 16% by weight PET fibers. In yet another example, the layer of cross-linked cellulose fibers may comprise from about 90 to about 100% by weight chemically cross-linked cellulose fibers.

Acquisition Layer

The ADS 50 may comprise an acquisition layer 52. The acquisition layer may be disposed between the distribution layer 54 and the topsheet 24. The acquisition layer 52 may be or may comprise a nonwoven material, such as a hydrophilic SMS or SMMS material, comprising a spunbonded, a melt-blown and a further spunbonded layer or alternatively a carded staple fiber chemical-bonded nonwoven. The nonwoven material may be latex bonded.

A further acquisition layer may be used in addition to a first acquisition layer described above. For example, a tissue layer may be placed between the first acquisition layer and the distribution layer. The tissue may have enhanced capillarity distribution properties compared to the acquisition layer described above.

Relationship between the Layers

Typically, adjacent layers and components may be joined together using conventional bonding methods, such as adhesive coating via slot coating or spraying on the whole or part of the surface of the layer, thermo-bonding, pressure bonding, or combinations thereof. This bonding is not represented in the Figures (except for the bonding between the raised elements of the leg cuffs 65 with the topsheet 24) for clarity and readability, but bonding between the layers of the article should be considered to be present unless specifically excluded. Adhesives may be used to improve the adhesion of the different layers between the backsheet 25 and the core wrap. The glue may be any suitable hot melt glue known in the art.

Fastening System

The absorbent article 20 may include a fastening system. The fastening system may be used to provide lateral tensions about the circumference of the absorbent article to hold the absorbent article on the wearer as is typical for taped diapers. The fastening system may comprise a male fastener that includes hooks, and a female fastening material that can includes loops for engaging the hooks of the male fastener. The outer cover layer 23 of the backsheet 21, as detailed above, is utilized as the female fastening material. Examples of male and female fasteners of fastening systems that are useful on the absorbent articles detailed herein are described in U.S. Patent Publication No. 2013/0123738, filed on Nov. 10, 2011.

Female Fastening Material

The following description relates to the female fastening material of the fastening system, which is integral to the outer cover 25 of the backsheet 21 (e.g., the outer cover of the backsheet is the female fastening material). Any of the following aspects of the female fastening material may be combined with any of the aspects of the bonding pattern of the outer cover layer 23 material that are detailed above.

Suitable nonwoven web materials useful in the present invention include, but are not limited to spunbond, melt-blown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. A suitable nonwoven web material may also be an SMS material, comprising a spunbonded, a melt-blown and a further spunbonded stratum or layer or any other combination of spunbonded and melt-blown layers, such as a SMMS or SSMMS etc. Examples include one or more layers of fibers with diameters below 1 micron (nanofibers and nanofiber layers); examples of these rise in combinations of SMS, SMNS, SSMNS or SMNMS nonwoven webs (where "N" designates a nanofiber layer). In some examples, permanently hydrophilic non-wovens, and in particular, nonwovens with durably hydrophilic coatings may be desirable. Typically, the suitable non-woven is air permeable. Typically the suitable nonwoven is water or liquid permeable, but may also be water impermeable by reason of fiber size and density, and hydrophobicity of the fibers. Water or liquid permeability may be enhanced by treatments to render the fibers hydrophilic, as discussed below.

The nonwoven web may be formed predominately of polymeric fibers. In some examples, suitable non-woven fiber materials may include, but are not limited to polymeric materials such as polyolefins, polyesters, polyamide, or specifically polypropylene (PP), polyethylene (PE), polylactic acid (PLA), polyethylene terephthalate (PET) and/or blends thereof. Nonwoven fibers may be formed of, or may include as additives or modifiers, components such as aliphatic polyesters, thermoplastic polysaccharides, or other biopolymers (bio-based or renewable polymers).

The individual fibers may be monocomponent or multi-component. The multicomponent fibers may be bicomponent, such as in a core-and-sheath or side-by-side arrangement. Often, the individual components comprise aliphatic polyolefins such as polypropylene or polyethylene, or their copolymers, aliphatic polyesters, thermoplastic polysaccharides or other biopolymers.

Figure 11A:
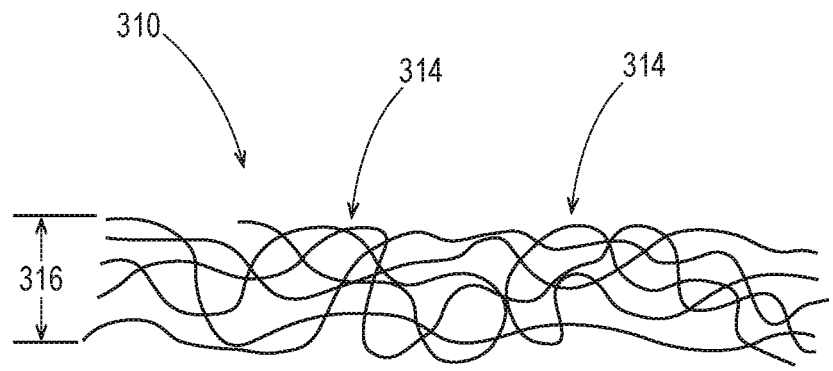
FIG. 11A is an enlarged side view of a portion of a female fastening material.
Figure 11B:
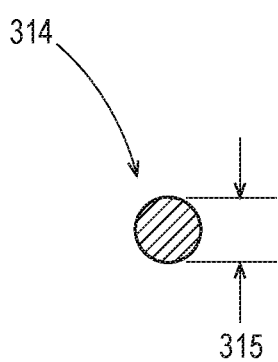
FIG. 11B is an enlarged cross-sectional view of a fiber from the female fastening material of FIG. 11A.

FIG. 11B is a further enlarged cross-sectional view of a fiber 314 from the female fastening material 310 of FIG. 11A. The fiber 314 has an overall fiber cross-sectional dimension 315. Since the shape of the fiber 314 is round, the overall cross-sectional shape of the fiber 314 is circular, and the overall fiber cross-sectional dimension 315 is the diameter of the circular overall cross-sectional shape of the fiber 314. For fibers with non-circular cross-sections, the overall fiber cross-sectional dimension is the largest distance measured linearly across the cross-section of the fiber. The overall fiber cross-sectional dimension of a fiber can be determined by making measurements on an enlarged image of the fiber, taken with equipment, at high magnification. For example, a Scanning Electron Microscope can be used.

The female fastening material 310 can include fibers of various sizes and shapes. For example, some or all of the fibers in the female fastening material 310 can have an overall cross-sectional dimension of 5-150 micrometers, or any integer value for micrometers between 5 and 150 micrometers, or any range formed by any of these values. As examples, the overall thickness can be less than 25 micrometers, less than 20 micrometers, or less than 15 micrometers or any range formed by any of these values. Also as an example, some or all of the fibers in the female fastening material 310 can have an overall cross-sectional shape that is circular, oval, squarish, rectangular, triangular, star-shaped, multi-lobal, or any other shape known in the art, or combinations of any of these. As an example, a fibrous material used as a female fastening material in a hook and loop fastening system, can be a nonwoven material made from bicomponent fibers, having an overall cross-sectional dimension of 17 micrometers and an overall cross-sectional shape that is round.

The landing zone area 44 is the portion of the garment facing surface of the outer cover layer 23 of the backsheet 21 where a traditional landing zone would generally be located. Accordingly, in the lateral dimension, the landing zone area 44 may span the width of the chassis W, or from the first side edge 3 to the second side edge 4 on the garment facing surface of the outer cover layer 23 of the backsheet 21. In a longitudinal dimension, the landing zone area 44 may begin about 25 mm inboard of the front waist edge 10 (or about 5 mm, 10 mm, 15 mm, or 20 mm inboard), and end about 70 mm inboard of the front waist edge (or about 50 mm, 55 mm, 60 mm, 65 mm, 75 mm, 80 mm, or 85 mm inboard) on the garment facing surface of the outer cover layer 23 of the backsheet 21.

Figure 16:
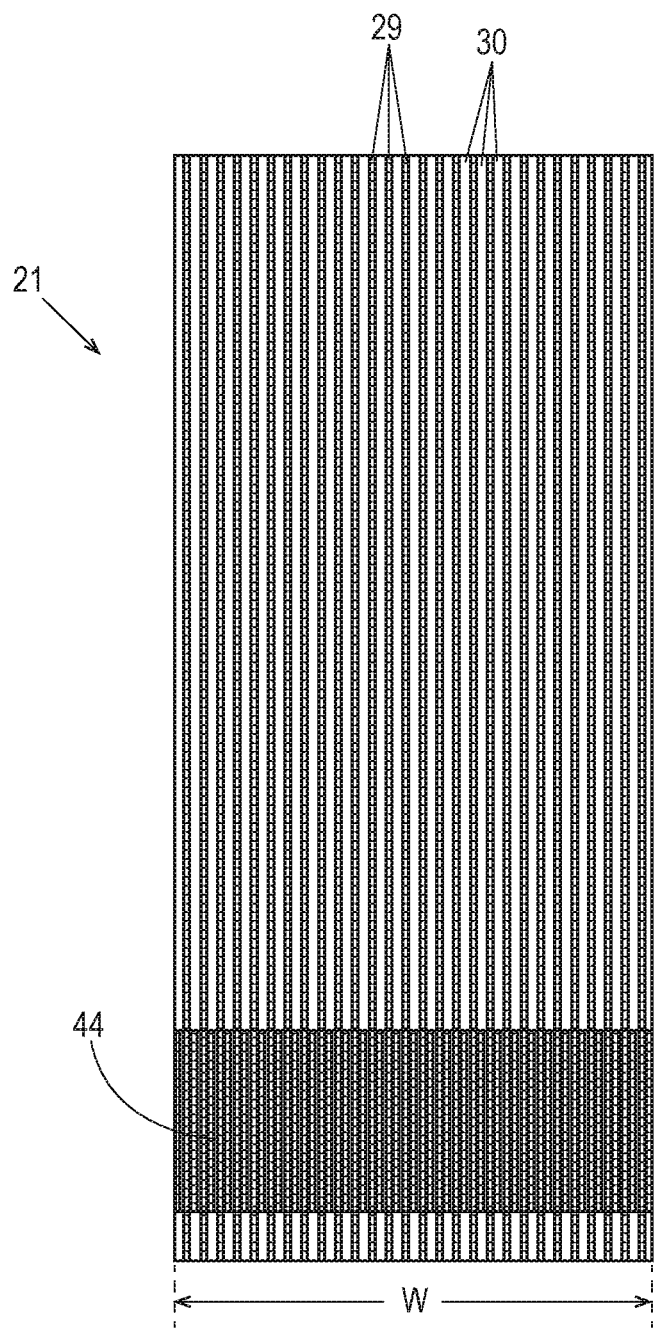
FIG. 16 is a top view of the backsheet of FIGS. 1-5, with the outer cover removed to illustrate the adhesive pattern on the garment facing surface of the film layer.
Figure 17:
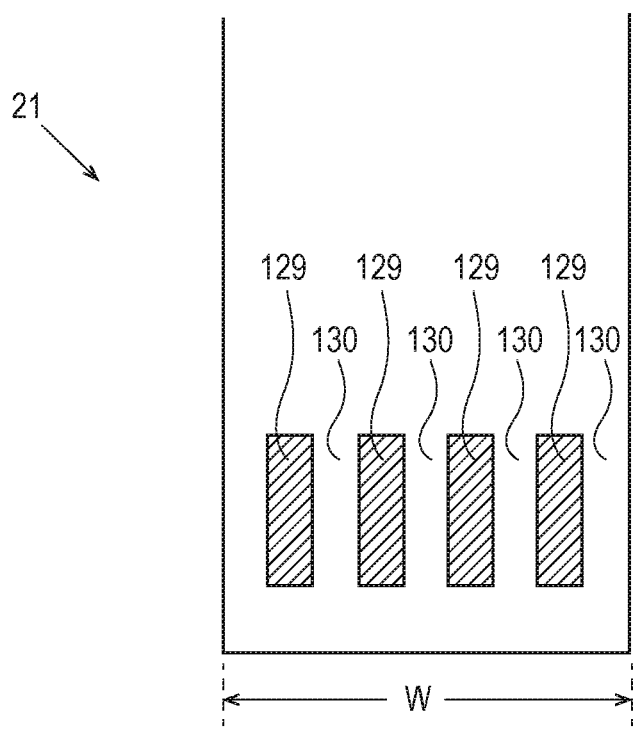
FIG. 17 is a top view of a backsheet with the outer cover layer removed to illustrate the adhesive pattern on the garment facing surface of the film layer.
Figure 18:
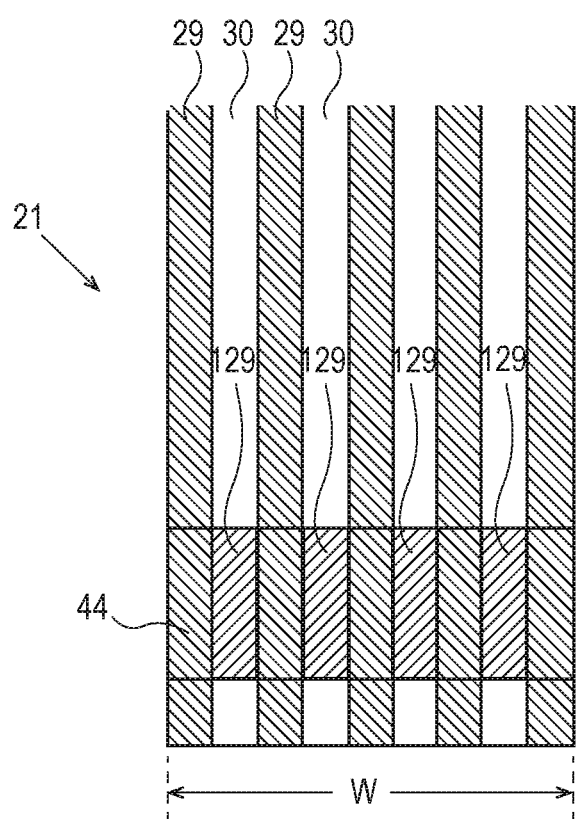
FIG. 18 is a top view of a backsheet with the outer cover layer removed to illustrate the adhesive pattern on the garment facing surface of the film layer.

In the landing zone area 44, the surface area coverage of adhesive on the garment facing side of the film layer 25 is increased when compared to the surface area coverage of adhesive on the garment facing side of the film layer outside of the landing zone area. As detailed above, a pattern of backsheet adhesive stripes may be used to join the film layer 25 and the outer cover layer 23 over the entire surface area of the garment facing surface of the film layer (or any portions of the surface area of the garment facing surface of the film layer outside of the landing zone area). Within the landing zone area 44, another adhesive application ("landing zone area adhesive" or "LZA adhesive") is used to provide additional adhesive surface area coverage on the garment facing surface of the film layer in the landing zone area. The LZA adhesive is applied between the film layer and the outer cover layer in the landing zone area 44 in a second pattern. For instance, if the first pattern of backsheet adhesive are 1.0 mm stripes of adhesive 29 adjacent to 1.0 mm wide adhesive-free sections 30 running in the longitudinal direction of the absorbent article over the surface area of the entire garment facing surface of the film layer 25, the LZA adhesive (applied only in the landing zone area 44) may be in a second pattern of a repeating unit of 1.0 mm wide stripes of adhesive 129 adjacent to 1.0 mm wide adhesive free sections 130, also running in the longitudinal direction of the absorbent article, and the 1.0 mm wide stripes of adhesive 129 are aligned with the 1.0 mm wide adhesive-free sections 30. Accordingly, the above detailed overall adhesive pattern (combining both the first and second patterns) will provide about 50% coverage for the surface area of the garment facing surface of the film layer (not including the landing zone area 44), and within the landing zone area, the coverage of the surface area of the garment facing surface of the film layer will be about 100%. Such an overall adhesive pattern is shown in FIGS. 16, 17, and 18 although the illustrations are not to scale in order to provide clarity. FIG. 17 shows only the second pattern of LZA adhesive, and FIGS. 16 and 18 show the overall pattern of adhesive, including both the first pattern of backsheet adhesive and the second pattern of LZA adhesive.

Figure 19A:
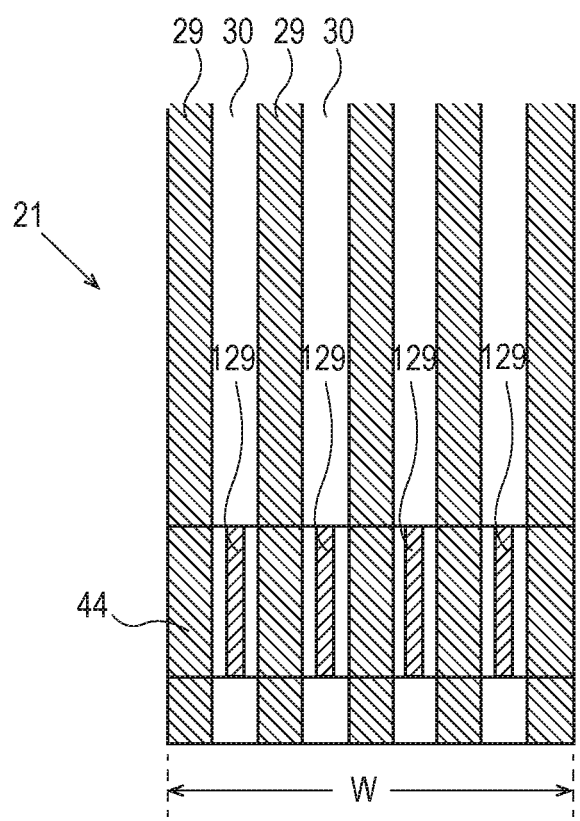
FIGS. 19A-C are a top views of a backsheet with the outer cover layer removed to illustrate the adhesive pattern on the garment facing surface of the film layer.
Figure 19B:
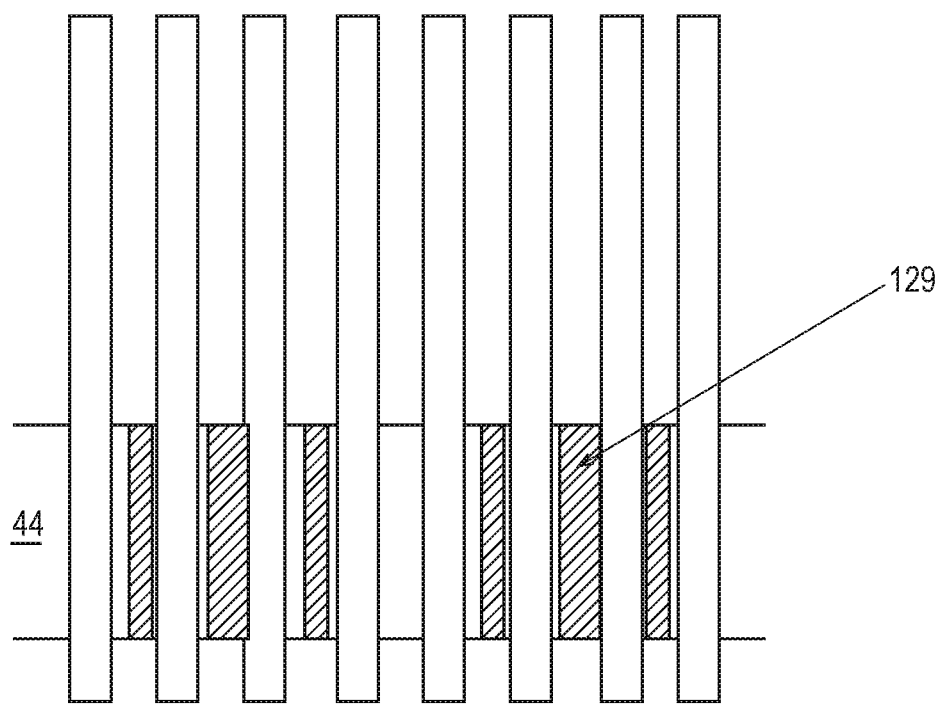
Figure 19C:
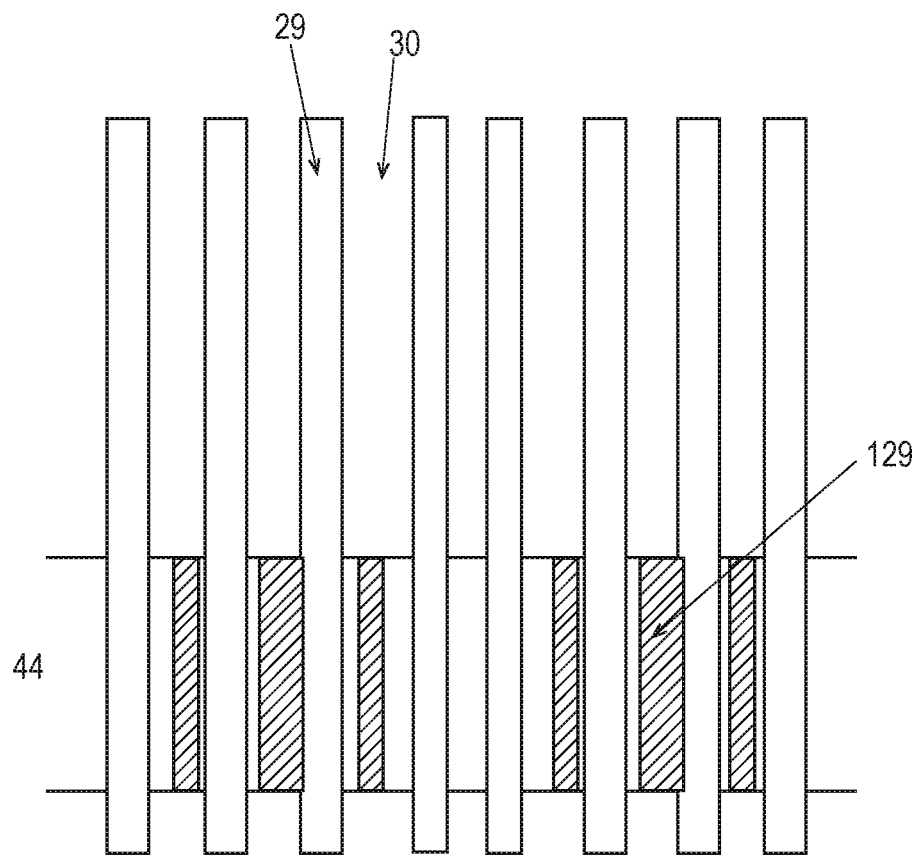
Figure 20:
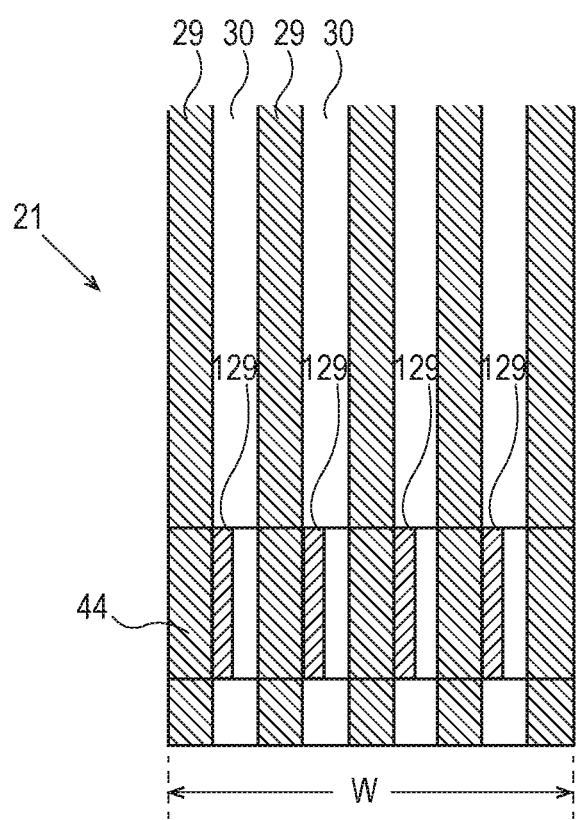
FIG. 20 is a top view of a backsheet with the outer cover layer removed to illustrate the adhesive pattern on the garment facing surface of the film layer.
Figure 21:
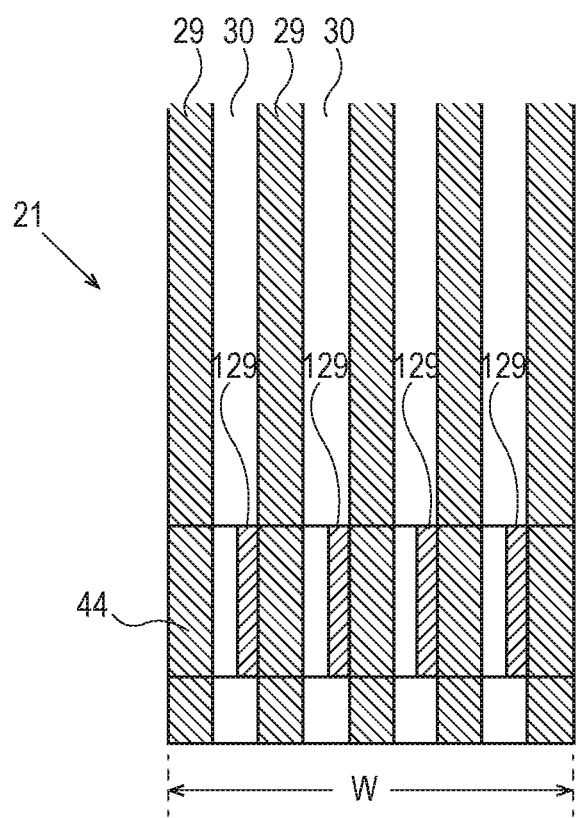
FIG. 21 is a top view of a backsheet with the outer cover layer removed to illustrate the adhesive pattern on the garment facing surface of the film layer.

Alternately, the first pattern of backsheet adhesive may be a pattern of 1.0 mm wide adhesive stripes 29 adjacent to 1.0 mm sections that are adhesive free 30 for the entire surface area of the garment facing surface of the film layer, and the second pattern of the LZA adhesive (applied only within the landing zone area 44) may be 0.5 mm wide adhesive stripes 129 adjacent to 1.0 mm wide adhesive-free sections 130, and aligned with the 1.0 mm wide adhesive-free sections 130, thus resulting in about 50% coverage for the surface area of the garment facing surface of the film layer (not including the landing zone area 44), and within the landing zone area, the coverage of the surface area of the garment facing surface of the film layer will be about 75%. Examples of such overall adhesive patterns are shown in FIG. 19-21, although the illustrations are not to scale in order to provide clarity. FIG. 19 shows a second pattern with adhesive stripes 129 centered in the 1.0 mm wide backsheet adhesive-free sections 30, FIG. 20 shows a second pattern with adhesive stripes 129 left justified in the 1.0 mm wide backsheet adhesive-free sections 30, and FIG. 21 shows a second pattern with adhesive stripes 129 right justified in the 1.0 mm wide backsheet adhesive-free sections 30. Other contemplated second adhesive patterns can have LZA adhesive located anywhere within the backsheet adhesive-free stripes 30. Examples of such adhesive patterns include zones of wider and narrower stripes (see FIG. 19a and FIG. 19b). Also the first pattern of the adhesive may have wider or narrower stripes (see FIG. 19c) but are not limited to the examples shown. Also the basis weight of the adhesive may vary in the individual stripes. Those variations may be used to optimize the softness and the integrity of the product in specific regions.

The above detailed second patterns for LZA adhesive will provide more than about 50% coverage of the surface area of the garment facing surface of the film layer 25 in the landing zone area 44. The second patterns for LZA adhesive may provide more than about 55%, more than about 60%, more than about 70%, more than about 75%, more than about 80%, more than about 85%, more than about 90%, more than about 95%, more than about 97%, more than about 99%, or about 100% adhesive surface area coverage in the landing zone area.

Although adhesive is exclusively taught in the examples above to bond the film layer 25 to the outer cover layer 23 to form the backsheet 21, other means of bonding that cover the particular surface area of garment facing surface of the film layer may be used in place of adhesive (within the landing zone area and/or outside of the landing zone area). Non-limiting examples include ultrasonic bonding, thermal bonding, compression bonding and combinations of thereof.

Male Fastener

Figure 12:
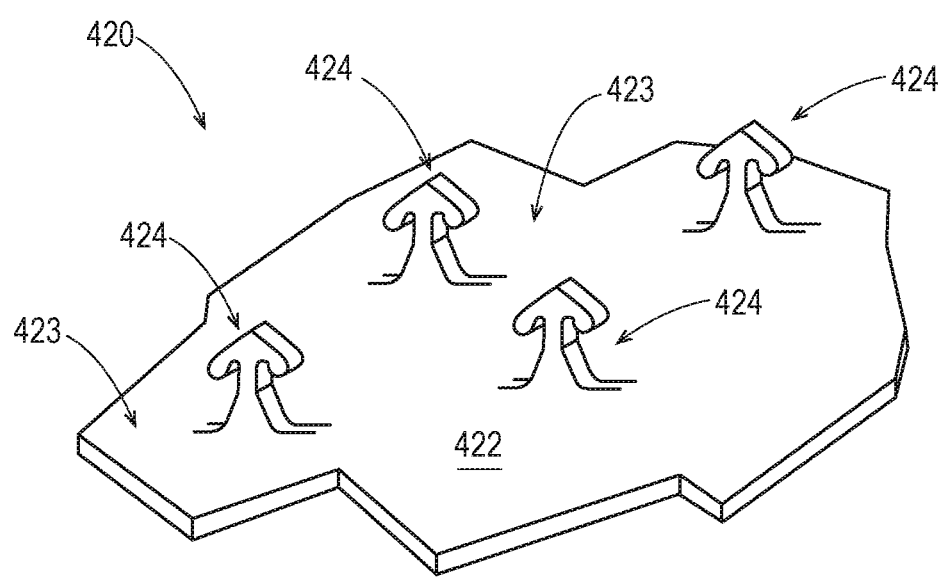
FIG. 12 is an enlarged isometric view of a portion of a male fastener.

FIG. 12 is an enlarged isometric view of a portion of a male fastening material 420. In FIG. 12, the portion is shown as broken away from a larger piece of material. The male fastening material 420 includes a plurality of bidirectional micro-sized hooks 424 disposed on a substrate 422 that has an overall planar shape. Each of the hooks 424 can be configured in the same way as the hook 530 of FIGS. 13A-13D, including any alternative embodiments. Alternatively the male fastening material 420 can also include one or more hooks configured in other ways. In the embodiment of FIG. 12, the hooks 424 and the substrate 422 are made from the same material, and the hooks 424 are a unified part of the substrate 422. The male fastening material 420 can be made from a wide variety of shapable and/or formable materials, including any of the natural or synthetic materials recited herein and/or any other suitable material suitable known in the art, in any workable combination, along with any additives or processing aids known in the art. As a particular example, the male fastening material 420 can be made from various renewable materials, including bioplastics derived from renewable biomass sources such as sugars, starches, cellulose, biopolymers, etc. In various alternate embodiments, the hooks and the substrate may be formed separately, or made from different materials.

The hooks 424 can be distributed across the male fastening material 420 in various patterns and hook densities. For example, the hooks 424 can be arranged in rows and/or columns, or any other arrangement of hooks known in the art. In various embodiments, the male fastening material can have a hook density of 10-1,000 hooks per square centimeter, or any integer number of hooks between 10 and 1,000, or any range formed by any of these values.

The male fastening material 420 and the hooks 424 thereon can be made by any suitable process known in the art. For example, the male fastening material can be made by casting, molding, profile extrusion, or microreplication.

FIG. 13A is an enlarged view of a front 532 of a bidirectional micro-sized hook 530 disposed on a top surface 523 of a portion of a substrate 522 of a male fastening material. In FIG. 13A, the portion of the substrate 522 is shown as broken away from a larger piece of material. The hook 530 is bidirectional since the cap 570 has two arms 580, extending from opposite sides 536 of the hook 530. The sides 536 of the hook are the outside portions of the hook 530, between a front 532 of the hook 530 and a back 534 of the hook 530. While the hook 530 is a bidirectional hook, it is contemplated that any of the structures, features, sizes, or dimensions of the hook 530 can be similarly applied to a unidirectional hook (one arm configured to hook in one direction) or to a multi-directional hook (more than two arms, with each arm configured to hook in a different direction).

FIG. 13A shows a cross-section of the hook 530 that has a width direction 547. This width direction 547 is parallel to the cross direction of the hook web. FIG. 13B shows a hook 530 that has a thickness direction 541, which is parallel to the substrate 522 and perpendicular to the width direction 547. This thickness direction 541 is also parallel to the longitudinal axis direction 80 of the absorbent article on FIG. 4.

In the embodiment of FIG. 13A, both of the arms 580 of the hook 530 are configured in the same way. However, it is also contemplated that any of the structures, features, sizes, or dimensions of an arm 580 of the hook 530 can be applied to one arm of a bidirectional hook, while the other arm can be configured in a different way. Further, it is contemplated that any of the structures, features, sizes, or dimensions of an arm 580 of the hook 530 can be applied to two or more arms of a multi-directional hook, while one or more other arms on that hook can be configured in one or more different ways.

The hook 530 includes a base 550, a stem 560, and a cap 570. The hook 530 also has sides 536. The hook 530 projects out from the substrate 522 in an upward direction 545, which is perpendicular to the substrate 522. The hook 530 also has a width direction 547. The width direction 547 is parallel to the overall planar shape of the substrate 522 and parallel to the largest linear dimension measured across the cap 570. In the embodiment of FIG. 13A, the width direction 547 is also parallel to the front 532 of the hook 530 and perpendicular to the sides 536. The hook 530 also has a thickness direction 541, which is parallel to the substrate 522 and perpendicular to the width direction 547. The thickness direction 541 is perpendicular to the page in FIG. 13A, so the thickness direction 541 is shown in FIGS. 13B and 13C. The thickness direction 541 is also parallel to the machine direction of the hook web and the longitudinal direction of the article 80 on FIG. 4.

Figure 13D:
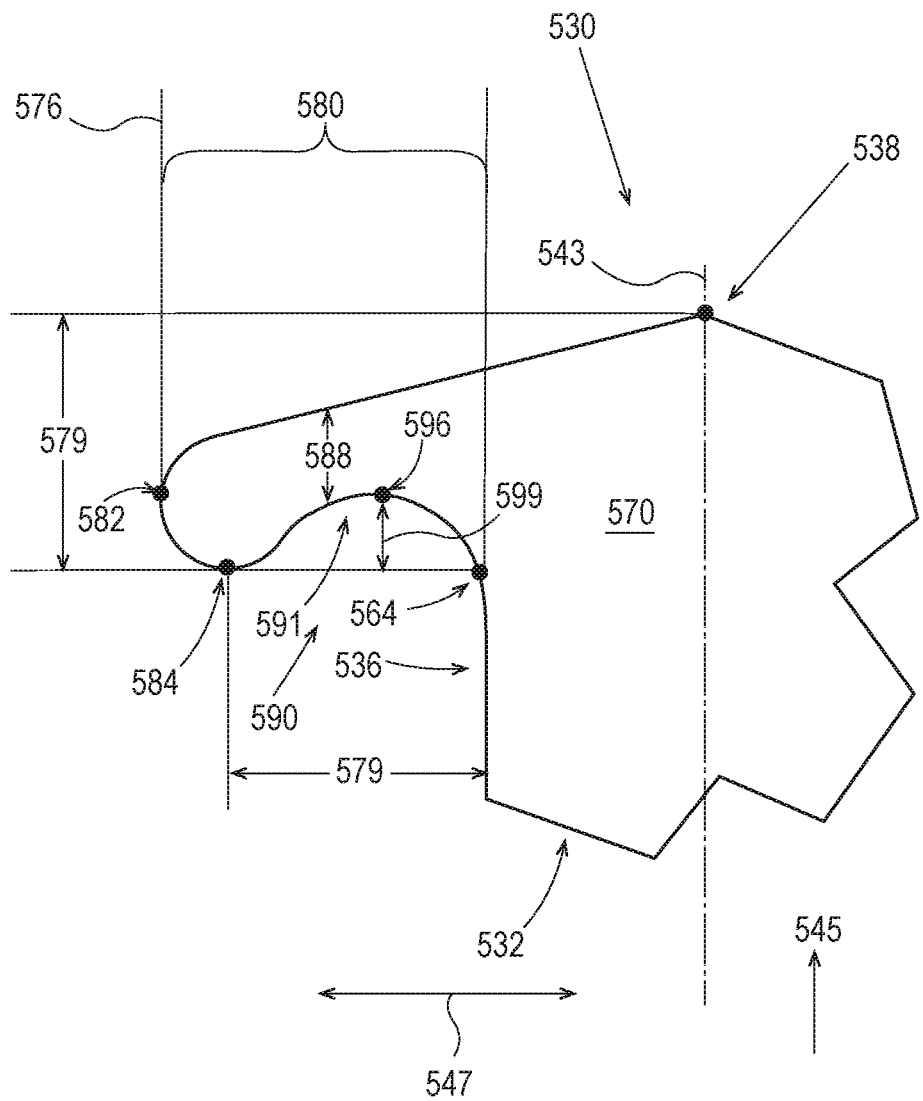
FIG. 13D is a further enlarged view of a portion of a front of the hook of FIG. 13A.

The base 550 is attached to the substrate 522, the stem 560 is attached to the base 550, and the cap 570 is attached to the stem 560. The cap 570 has an overall cap height 579, which is measured as described in connection with FIG. 13D. The hook 530 also has an overall hook height 539 measured linearly in the upward direction 545 from the top surface 523 of the substrate 522 to a highest point on the outer surface of the hook 530 (farthest away from the top surface 523 of the substrate 522). In the embodiment of FIG. 13A, a peak 538 of the cap 570 is the highest point on the outer surface of the hook 530. The hook 530 also has a central axis 543, which passes through the center of the hook. In the embodiment of FIG. 13A, the central axis 543 is aligned with the upward direction 545, however, in various embodiments, the central axis 543 may not be perpendicular with respect to the substrate 522; that is the hook may be tipped in the width direction 547 and/or the thickness direction 541. Also, in various embodiments the cap 570 may not have a peak, but may have a rounded top, or a flat top, or a recessed top, or any other shape known in the art or combinations of any of these.

The front edge 572, the back edge 574, and the side edges 576 together, when viewed from above the peak 538 of the hook 530, define a vertical engagement effective area 577. The vertical effective engagement area 577 has a width-to-thickness aspect ratio, which is defined as the widest overall width of the vertical engagement effective area 577 divided by the thickest overall thickness of the vertical engagement effective area 577. The width-to-thickness aspect ratio can be 1-2, or any value in increments of 0.01 between 1 and 2, or any range formed by any of these values. As examples, the width-to-thickness aspect ratio can be 1.2, 1.3, 1.6, 1.8, or 1.9, or any range formed by any of these values. The size of the vertical effective engagement area 577 can be 40,000-120,000 square micrometers, or any value in increments of 5,000 square micrometers between 40,000 and 120,000 square micrometers, or any range formed by any of these values. As examples, the vertical effective engagement area 577 can be 40,000, 50,000, 60,000, 90,000, 100,000, or 120,000 square micrometers, or any range formed by any of these values.

The recessed portion 591 has an overall recessed width 597 measured linearly in the width direction 547 from the lowest point 584 on the arm 580 (as described above) to the side point 564. When the hook 530 is used on a male fastening material of a fastening system, and the fastening system uses a fibrous material as the female fastening material, the overall recessed width 597 can be sized to the overall fiber cross-sectional dimension of the fibrous material, such as the overall fiber cross-sectional dimension 315 of the fiber 314 of the female fastening material 310. The overall recessed width 597 can be 200-500% of the overall fiber cross-sectional dimension, or any integer value of percentage between 200% and 500% of the overall fiber cross-sectional dimension, or any range formed by any of these values. As examples, the overall recessed width 597 can be 200%, 300%, 400%, or 500% of the overall fiber cross-sectional dimension, or any range formed by any of these values. While not wishing to be bound by this theory, it is believed that, selecting these relative dimensions for the overall recessed width 597, as described above, allow two to five fibers to fit in the recessed portion 591, which increases the likelihood that fibers can be retained by the hook 530.

When the hook 530 is used on a male fastening material of a fastening system, and the fastening system uses a fibrous material as the female fastening material, the deepest recessed depth 599 can be sized to the overall fiber cross-sectional dimension of the fibrous material, such as the overall fiber cross-sectional dimension 315 of the fiber 314 of the female fastening material 310. The deepest recessed depth 599 can be 40-200% of the overall fiber cross-sectional dimension, or any integer value of percentage between 40% and 200% of the overall fiber cross-sectional dimension, or any range formed by any of these values. As examples, the deepest recessed depth 599 can be 50%, 60%, 100%, or 150% of the overall fiber cross-sectional dimension, or any range formed by any of these values. While not wishing to be bound by this theory, it is believed that, selecting these relative dimensions for the deepest recessed depth 599, as described above, allows one or more fibers to fit in the recessed portion 591, and increases the likelihood that fibers will be retained by the hook 530.

The deepest recessed depth 599 can also be sized in relation to the overall cap height 579. The deepest recessed depth 599 can be 10-60% of the overall cap height 579, or any integer value of percentage between 10% and 50% of the overall cap height 579, or any range formed by any of these values. As examples, the deepest recessed depth 599 can be 10%, 20%, 50%, or 60% of the overall cap height 579, or any range formed by any of these values.

Front and Rear Ears

The absorbent article may comprise front ears 46 and rear ears 40. The ears may be an integral part of the chassis, such as formed from the topsheet 24 and/or backsheet 21 as side panels. Alternatively, as represented on FIG. 1, the ears may be separate elements attached to the chassis by gluing, heat embossing, and/or pressure bonding. The rear ears 40 may be stretchable to facilitate the attachment of the tabs 42 to the landing zone area 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Packaging:

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

FIG. 22 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 22). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

EXAMPLES

A. An absorbent article comprising:
   a) a chassis having i) a topsheet, ii) a backsheet comprising a film layer and an outer cover layer, and iii) an absorbent core disposed between the topsheet and the backsheet; and
   b) a fastening system, the fastening system having a male fastener and a female fastening material, wherein the female fastening material is comprised of a portion of the outer cover layer that is located in a landing zone area;
   wherein the film layer and the outer cover layer are joined together through a backsheet adhesive applied in a first pattern; and in the landing zone area, the film layer and the outer cover layer are joined together through an additional LZA adhesive applied in a second pattern.
B. The absorbent article of Paragraph A, wherein the backsheet adhesive covers between 30% and 70% of the surface area of the garment facing surface of the film layer.
C. The absorbent article of any one of Paragraphs A-B, wherein the backsheet adhesive covers 50% of the surface area of the garment facing surface of the film layer.
D. The absorbent article of any one of Paragraphs A-C, wherein the LZA adhesive covers between 30% and 70% of the surface area of the garment facing surface of the film layer within the landing zone area.
E. The absorbent article of any one of Paragraphs A-D, wherein the backsheet adhesive and the LZA adhesive combine to cover between 80% and 100% of the surface area of the garment facing surface of the film layer within the landing zone area.
F. The absorbent article of any one of Paragraphs A-E, wherein the backsheet adhesive covers between 30% and 70% of the surface area of the garment facing surface of the film layer outside of the landing zone area.
G. The absorbent article of any one of Paragraphs A-F, wherein the backsheet adhesive and the LZA adhesive combine to cover at least 90% of the surface area of the garment facing surface of the film layer within the landing zone area.
H. The absorbent article of any one of Paragraphs A-G, wherein the backsheet adhesive and the LZA adhesive combine to cover at least 95% of the surface area of the garment facing surface of the film layer within the landing zone area.
I. The absorbent article of any one of Paragraphs A-H, wherein the first pattern comprises stripes of backsheet adhesive running in the longitudinal direction of the absorbent article.
J. The absorbent article of any one of Paragraphs A-I, wherein the first pattern comprises a repeating unit of: a 1.0 mm wide stripe of backsheet adhesive running in the longitudinal direction of the absorbent article, followed by a 1.0 mm wide stripe that is free of backsheet adhesive running in the longitudinal direction of the absorbent article.
K. The absorbent article of any one of Paragraphs A-J, wherein the second pattern comprises stripes of LZA adhesive running in the longitudinal direction of the absorbent article.
L. The absorbent article of any one of Paragraphs A-K, wherein the second pattern comprises a repeating unit of: a 1.0 mm wide stripe of LZA adhesive running in the longitudinal direction of the absorbent article, followed by a 1.0 mm wide stripe that is free of LZA adhesive running in the longitudinal direction of the absorbent article.
M. The absorbent article of any one of Paragraphs A-L, wherein the 1.0 mm wide stripes of LZA adhesive running in the longitudinal direction of the absorbent article substantially align with the 1.0 mm wide stripes that are free of backsheet adhesive running in the longitudinal direction of the absorbent article.
N. The absorbent article of any one of Paragraphs A-M, wherein a separate, stretchable ear is attached to the chassis and the male fastener is attached to the separate, stretchable ear.
O. An absorbent article comprising:
   a) a chassis having i) a topsheet, ii) a backsheet comprising a film layer and an outer cover layer, and iii) an absorbent core disposed between the topsheet and the backsheet;
   b) a pair of separate, stretchable ears attached to the chassis; and
   c) a fastening system, the fastening system having a male fastener and a female fastening material, wherein the female fastening material is comprised of a portion of the outer cover layer that is located in a landing zone area;
   wherein the film layer and the outer cover layer are joined together through a backsheet adhesive applied in a first pattern; and in the landing zone area, the film layer and the outer cover layer are joined together through an additional LZA adhesive applied in a second pattern;
   wherein the backsheet adhesive covers between 30% and 70% of the surface area of the garment facing surface of the film layer;
   wherein the backsheet adhesive and the LZA adhesive combine to cover between 80% and 100% of the surface area of the garment facing surface of the film layer within the landing zone area.
P. The absorbent article of Paragraph O, wherein the backsheet adhesive and the LZA adhesive combine to cover at least 95% of the surface area of the garment facing surface of the film layer within the landing zone area.
Q. The absorbent article of any one of Paragraphs O-P, wherein the first pattern comprises stripes of backsheet adhesive running in the longitudinal direction of the absorbent article.
R. The absorbent article of any one of Paragraphs O-Q, wherein the first pattern comprises a repeating unit of: a 1.0 mm wide stripe of backsheet adhesive running in the longitudinal direction of the absorbent article, followed by a 1.0 mm wide stripe that is free of backsheet adhesive running in the longitudinal direction of the absorbent article.
S. The absorbent article of any one of Paragraphs O-R, wherein the second pattern comprises stripes of LZA adhesive running in the longitudinal direction of the absorbent article.
T. The absorbent article of any one of Paragraphs O-S, wherein the second pattern comprises a repeating unit of: a 1.0 mm wide stripe of LZA adhesive running in the longitudinal direction of the absorbent article, followed by a 1.0 mm wide stripe that is free of LZA adhesive running in the longitudinal direction of the absorbent article.

U. The absorbent article of any one of Paragraphs O-T, wherein the 1.0 mm wide stripes of LZA adhesive running in the longitudinal direction of the absorbent article substantially align with the 1.0 mm wide stripes that are free of backsheet adhesive running in the longitudinal direction of the absorbent article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
    a) a chassis having i) a topsheet, ii) a backsheet comprising a film layer and an outer cover layer, and iii) an absorbent core disposed between the topsheet and the backsheet; and
    b) a fastening system, the fastening system comprising a male fastener and a female fastening material, wherein the female fastening material is comprised of a portion of the outer cover layer that is located in a landing zone area;
    wherein the film layer and the outer cover layer are joined together through a backsheet adhesive applied in a first pattern; and in the landing zone area, the film layer and the outer cover layer are joined together through an additional LZA adhesive applied in a second pattern.

2. The absorbent article of claim 1, wherein the backsheet adhesive covers between about 30% and about 70% of a surface area of a garment facing surface of the film layer.

3. The absorbent article of claim 2, wherein the backsheet adhesive covers at least about 50% of the surface area of the garment facing surface of the film layer.

4. The absorbent article of claim 1, wherein the LZA adhesive covers between about 30% and about 70% of a surface area of a garment facing surface of the film layer within the landing zone area.

5. The absorbent article of claim 1, wherein the backsheet adhesive and the LZA adhesive combine to cover between about 80% and about 100% of a surface area of the a garment facing surface of the film layer within the landing zone area.

6. The absorbent article of claim 5, wherein the backsheet adhesive covers between about 30% and about 70% of the surface area of the garment facing surface of the film layer outside of the landing zone area.

7. The absorbent article of claim 1, wherein the backsheet adhesive and the LZA adhesive combine to cover at least about 90% of a surface area of a garment facing surface of the film layer within the landing zone area.

8. The absorbent article of claim 1, wherein the backsheet adhesive and the LZA adhesive combine to cover at least about 95% of a surface area of a garment facing surface of the film layer within the landing zone area.

9. The absorbent article of claim 1, wherein the first pattern comprises stripes of backsheet adhesive running in a longitudinal direction of the absorbent article.

10. The absorbent article of claim 1, wherein the first pattern comprises a repeating unit of: a 1.0 mm wide stripe of backsheet adhesive running in a longitudinal direction of the absorbent article, followed by a 1.0 mm wide stripe that is free of backsheet adhesive running in the longitudinal direction of the absorbent article.

11. The absorbent article of claim 10, wherein the second pattern comprises stripes of LZA adhesive running in the longitudinal direction of the absorbent article.

12. The absorbent article of claim 11, wherein the second pattern comprises a repeating unit of: a 1.0 mm wide stripe of LZA adhesive running in the longitudinal direction of the absorbent article, followed by a 1.0 mm wide stripe that is free of LZA adhesive running in the longitudinal direction of the absorbent article.

13. The absorbent article of claim 12, wherein the 1.0 mm wide stripes of LZA adhesive running in the longitudinal direction of the absorbent article substantially align with the 1.0 mm wide stripes that are free of backsheet adhesive running in the longitudinal direction of the absorbent article.

14. The absorbent article of claim 1, wherein a separate, stretchable ear is attached to the chassis and the male fastener is attached to the separate, stretchable ear.

15. An absorbent article comprising:
    a) a chassis having i) a topsheet, ii) a backsheet comprising a film layer and an outer cover layer, and iii) an absorbent core disposed between the topsheet and the backsheet;
    b) a pair of separate, stretchable ears attached to the chassis; and
    c) a fastening system, the fastening system comprising a male fastener and a female fastening material, wherein the female fastening material is comprised of a portion of the outer cover layer that is located in a landing zone area;
    wherein the film layer and the outer cover layer are joined together through a backsheet adhesive applied in a first pattern; and in the landing zone area, the film layer and the outer cover layer are joined together through an additional LZA adhesive applied in a second pattern;
    wherein the backsheet adhesive covers between about 30% and about 70% of the a surface area of a garment facing surface of the film layer;
    wherein the backsheet adhesive and the LZA adhesive combine to cover between about 80% and about 100% of the surface area of the garment facing surface of the film layer within the landing zone area.

16. The absorbent article of claim 15, wherein the backsheet adhesive and the LZA adhesive combine to cover at least about 95% of the surface area of the garment facing surface of the film layer within the landing zone area.

17. The absorbent article of claim 15, wherein the first pattern comprises stripes of backsheet adhesive running in a longitudinal direction of the absorbent article.

18. The absorbent article of claim 15, wherein the first pattern comprises a repeating unit of: a 1.0 mm wide stripe of backsheet adhesive running in the a longitudinal direction of the absorbent article, followed by a 1.0 mm wide stripe that is free of backsheet adhesive running in the longitudinal direction of the absorbent article.

19. The absorbent article of claim 18, wherein the second pattern comprises stripes of LZA adhesive running in the longitudinal direction of the absorbent article.

20. The absorbent article of claim 19, wherein the second pattern comprises a repeating unit of: a 1.0 mm wide stripe of LZA adhesive running in the longitudinal direction of the absorbent article, followed by a 1.0 mm wide stripe that is free of LZA adhesive running in the longitudinal direction of the absorbent article.

21. The absorbent article of claim 20, wherein the 1.0 mm wide stripes of LZA adhesive running in the longitudinal direction of the absorbent article substantially align with the 1.0 mm wide stripes that are free of backsheet adhesive running in the longitudinal direction of the absorbent article.

\* \* \* \* \*